United States Patent
Hibner et al.

(10) Patent No.: US 10,743,898 B2
(45) Date of Patent: Aug. 18, 2020

(54) SURGICAL DEVICES HAVING POWER-ASSISTED JAW CLOSURE AND METHODS FOR COMPRESSING AND SENSING TISSUE

(71) Applicant: Ethicon LLC, Guaynabo, PR (US)

(72) Inventors: John A. Hibner, Mason, OH (US); Catherine A. Corbett, Cincinnati, OH (US); Scott R. Bingham, Mason, OH (US); Chad P. Boudreaux, Cincinnati, OH (US); Carl J. Draginoff, Jr., Mason, OH (US); Geoffrey S. Strobl, Williamsburg, OH (US); Eric N. Johnson, Maineville, OH (US)

(73) Assignee: Ethicon LLC, Guaynabo, PR (US)

( * ) Notice: Subject to any disclaimer, the term of this patent is extended or adjusted under 35 U.S.C. 154(b) by 4 days.

(21) Appl. No.: 16/030,062

(22) Filed: Jul. 9, 2018

(65) Prior Publication Data
US 2019/0000495 A1   Jan. 3, 2019

Related U.S. Application Data

(62) Division of application No. 14/503,045, filed on Sep. 30, 2014, now Pat. No. 10,039,564.

(51) Int. Cl.
*A61B 18/00* (2006.01)
*A61B 17/285* (2006.01)
(Continued)

(52) U.S. Cl.
CPC .......... *A61B 17/285* (2013.01); *A61B 17/282* (2013.01); *A61B 18/1445* (2013.01);
(Continued)

(58) Field of Classification Search
CPC . A61B 17/285; A61B 18/1445; A61B 17/282; A61B 2018/00702;
(Continued)

(56) References Cited

U.S. PATENT DOCUMENTS

| 2004/0232197 A1 | 11/2004 | Shelton et al. |
| 2012/0022527 A1 | 1/2012 | Woodruff et al. |

(Continued)

FOREIGN PATENT DOCUMENTS

| EP | 2243493 A1 | 10/2010 |
| WO | WO-2015/116400 A1 | 8/2015 |

OTHER PUBLICATIONS

International Search Report and Written Opinion for Application No. PCT/US2015/052623, dated Feb. 18, 2016 (19 pages).

*Primary Examiner* — Scott M. Getzow
(74) *Attorney, Agent, or Firm* — Mintz Levin Cohn Ferris Glovsky and Popeo, P.C.

(57) ABSTRACT

Surgical devices are provided having power-assisted or fully powered jaw closure. The devices herein generally include a handle portion, an elongate shaft, and an effector having first and second jaws configured to engage tissue. A motor and one or more compression springs can be operatively coupled, and activation of the motor can compress the spring(s) to reduce the amount of user supplied force to compress tissue between the jaws. In some embodiments, the devices can be configured to regulate an amount of compression applied by the jaws prior to, during, and/or after cutting of the tissue to promote hemostasis. For example, the devices can include sensors, processors, and/or other components that analyze data indicative of tissue type and tissue load. Based on this feedback, the device can automatically adjust the amount of compression or energy applied to the tissue to seal the tissue.

16 Claims, 20 Drawing Sheets

(51) Int. Cl.
*A61B 17/28* (2006.01)
*A61B 18/14* (2006.01)
*A61B 17/00* (2006.01)
*A61B 90/00* (2016.01)

(52) U.S. Cl.
CPC ............... *A61B 2017/00039* (2013.01); *A61B 2017/00075* (2013.01); *A61B 2017/00398* (2013.01); *A61B 2018/00428* (2013.01); *A61B 2018/00607* (2013.01); *A61B 2018/00642* (2013.01); *A61B 2018/00702* (2013.01); *A61B 2018/1455* (2013.01); *A61B 2090/065* (2016.02)

(58) Field of Classification Search
CPC ........... A61B 2018/00642; A61B 2018/00607; A61B 2018/00428; A61B 2017/00075; A61B 2017/00039; A61B 2090/065; A61B 2018/1455; A61B 2017/00398
See application file for complete search history.

(56) References Cited

U.S. PATENT DOCUMENTS

| | | |
|---|---|---|
| 2012/0083783 A1 | 4/2012 | Davison et al. |
| 2013/0161374 A1 | 6/2013 | Swayze et al. |
| 2015/0190191 A1 | 7/2015 | Strobl |
| 2015/0209059 A1* | 7/2015 | Trees ................ A61B 18/1445 606/170 |
| 2016/0089175 A1 | 3/2016 | Hibner et al. |

* cited by examiner

SURGICAL DEVICES HAVING POWER-ASSISTED JAW CLOSURE AND METHODS FOR COMPRESSING AND SENSING TISSUE

CROSS REFERENCE TO RELATED APPLICATIONS

The present application is a divisional of U.S. patent application Ser. No. 14/503,045 (now U.S. Pat. No. 10,039, 564) entitled "Surgical Devices Having Power-Assisted Jaw Closure and Methods for Compressing and Sensing Tissue" filed Sep. 30, 2014, which is hereby incorporated by reference in its entirety.

FIELD

The present invention relates to surgical devices and methods for compressing tissue, and sensing tissue and other objects grasped by the device.

BACKGROUND

Surgical devices are used in various open, endoscopic, and laparoscopic surgeries to transect tissue volumes and blood vessels. The devices generally include jaws for grasping tissue therebetween and a cutting mechanism that is advanced through the grasped tissue to transect it. The cutting mechanism can be designed to travel within a track formed in one or both jaws of the cutting mechanism. In some instances the devices can also be used to seal tissue volumes and blood vessels being transected, for instance by applying electrical energy to the grasped tissue to seal it before tissue transection is completed. For example, various mono-polar and bi-polar radio frequency (RF) surgical instruments and surgical techniques have been developed for sealing tissue volumes and blood vessels. Electrodes can be disposed on a face of one or both of the jaws and can apply energy to the grasped tissue to promote hemostasis.

Some of these surgical devices incorporate mechanical linkages between the closure actuator and the jaws such that when a user manipulates the closure actuator, e.g., by manually squeezing a trigger, the jaws close. This can give a user control over the amount of compression applied to tissue in the jaws because the user receives tactile feedback when operating the closure actuator. However, high manual forces may be necessary for a user to operate the closure actuator in a mechanically-based device and there are limits as to the amount of compression that can be achieved manually.

Further, when operating a tissue compression device, an amount of compression applied by the jaws to the tissue affects hemostasis. By increasing the amount of compression applied to the target tissue, the flow of blood can be limited, which can decrease the time necessary to achieve hemostasis. However, applying too much compression to manipulate tissue without sealing the tissue can result in damage to the tissue if the applied compression/clamping force is too high. Additionally, applying too much compression can artificially reduce impedance of the tissue as a result of being overcompressed and too thin. Overcompression can also make it difficult to apply resistive heating to tissue using an RF tissue sealing device. An optimal amount of force depends on various factors, including the type and thickness of tissue disposed between the jaws.

Accordingly, there remains a need for improved surgical devices and methods for compressing tissue and sensing tissue and other objects grasped by the device.

SUMMARY

Surgical devices, systems, and methods for compressing tissue and/or sensing tissue and other objects grasped by the device are provided herein. In one embodiment, a surgical instrument includes a jaw assembly having a first jaw and a second jaw pivotally coupled together. The first and second jaws can have opposed tissue contacting surfaces configured to pivot towards each other to compress tissue therebetween when a force applied to at least one of the first and second jaws meets or exceeds a threshold force. A cutting member having a distal portion thereof can be disposed between the opposed tissue contacting surfaces of the first and second jaws, the distal portion including a cutting edge that extends between and substantially perpendicular to the first and second jaws. The device can further include a housing having a motor and a first spring disposed therein, the motor being operatively coupled to the first spring such that the motor is configured to move the first spring from a first position to a second, compressed position to increase a force the jaws apply to the tissue, and the motor further being operatively coupled to the cutting member such that the motor is configured to drive the cutting member distally through the first and second jaws.

A second spring can be operatively coupled to a closure actuator disposed in the housing such that when the closure actuator is activated, the second spring moves from a first position to a second, compressed position and the jaws apply a compressive force to the tissue. In some embodiments, the compressive force can be greater than a force applied to the closure actuator. The motor can be operatively coupled to the jaws such that activation of the motor is configured to close the jaws prior to the cutting member being advanced distally through the first and second jaws. The device can include a drive mechanism operatively coupling the motor to the first spring, the drive mechanism including a lead screw having first and second threaded portions, the first threaded portion coupled to a first driving member for compressing the first spring and the second threaded portion coupled to a second driving member for advancing the cutting member within the jaws. In certain aspects, the second driving member includes a rack and first and second pinions coupled to the first spring such that when the motor is activated, the lead screw rotates and moves the second driving member distally toward the jaws. Distal movement of the driving member can be configured to rotate first and second pinions which move a distal end of the first spring proximally away from the jaws to compress the first spring.

In certain aspects, the device can include a spring-loaded bendix mechanism having a compression gear and a blade advancing gear spaced axially apart, the bendix mechanism being configured to move away from the motor when the motor is activated, and the axial spacing between the compression gear and the blade advancing gear increasing during activation of the motor. A rotatable housing and a translation mechanism can be configured so that activation of the motor rotates the rotatable housing which moves the translation mechanism distally to compress the first spring.

The device can have a shaft extending between the housing and the jaw assembly and including a jaw closure tube having a proximal end operatively coupled to the second spring and a distal end coupled to a proximal end of the jaw assembly. In certain aspects, a cutting member advancing tube can be disposed in the shaft and having a proximal end operatively coupled to the first compression spring and a distal end coupled to a proximal end of the cutting member. In certain aspects, the device can include a compression spring in series with a counterbalance spring such that activation of the motor decreases compression on the counterbalance spring and increases compression of the compression spring to compress tissue disposed in the jaws.

In another embodiment, a surgical device can include a proximal handle portion that includes a motor and an actuator operatively coupled to the motor, an elongate shaft extending distally from the handle portion, an end effector, and a cutting element. The end effector can have first and second jaws pivotably coupled to each other with at least one of the first and second jaws being coupled to a distal end of the elongate shaft, at least one of the first and second jaws including an electrode configured to apply energy to tissue disposed between the jaws. The cutting element can be disposed between the jaws and can be operatively coupled to the motor. The device can further include a tissue-determining sensor configured to measure one or more mechanical parameters that change based on the type of tissue or other object disposed between the jaws to determine the type of tissue or object disposed between the jaws. A controller can be configured to adjust at least one parameter, such as a speed of the cutting element and/or an amount of energy applied by the electrode to tissue disposed between the jaws based on the one or more mechanical parameters measured by the tissue-determining sensor.

The device can vary in any number of ways. For example, the device can include a processor configured to analyze a change in distance between the jaws for a given change in force applied to the tissue disposed in the jaws and to determine a tissue-spring rate, the processor being configured to determine the type of tissue or object disposed between the jaws based on the tissue-spring rate. The change in distance between the jaws can be determined based on a torque of the motor. In certain aspects, a compression spring can be in series with a counterbalance spring such that activation of the motor decreases compression on the counterbalance spring and increases compression of the compression spring to compress tissue disposed in the jaws. Activation of the motor can be configured to close the jaws and to advance the cutting member within the jaws to cut tissue disposed therebetween. The cutting member can be disposed on a distal end of an I-shaped compression member.

A surgical method is provided that can include positioning tissue between first and second jaws of an end effector of a surgical device, opening and closing the jaws at least two times such that a cyclical compression force is applied to the tissue disposed therebetween, and measuring the applied compression force over time. The method can further include determining a tissue spring rate based on the applied compression force and a change in distance between the jaws when the jaws move between the opened and closed positions, and modulating an amount of the power supplied to the motor based on the tissue spring rate so as to adjust a speed of a cutting element that travels through the tissue disposed between the first and second jaws.

In certain aspects, energy can be applied to the tissue disposed in the jaws to seal the tissue. In other aspects, the jaws can be opened and closed repeatedly along the tissue seal so that a tissue spring rate of the seal is determined. A change in distance between the jaws from the opened to the closed positions can be determined using a Hall Effect sensor. In other embodiments, a proximity sensor, switch, potentiometer, encoder, or other similar devices can be used to determine a change in distance between the jaws from the opened to the closed positions.

BRIEF DESCRIPTION OF THE DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the various embodiments generally have similar features when those components are of a similar nature and/or serve a similar purpose. Additionally, to the extent features or sides of a structure are described herein as being a "first feature" or "first side" or a "second feature" or "second side," such numerical ordering is generally arbitrary, and thus such numbering can be interchangeable.

Figure 2:
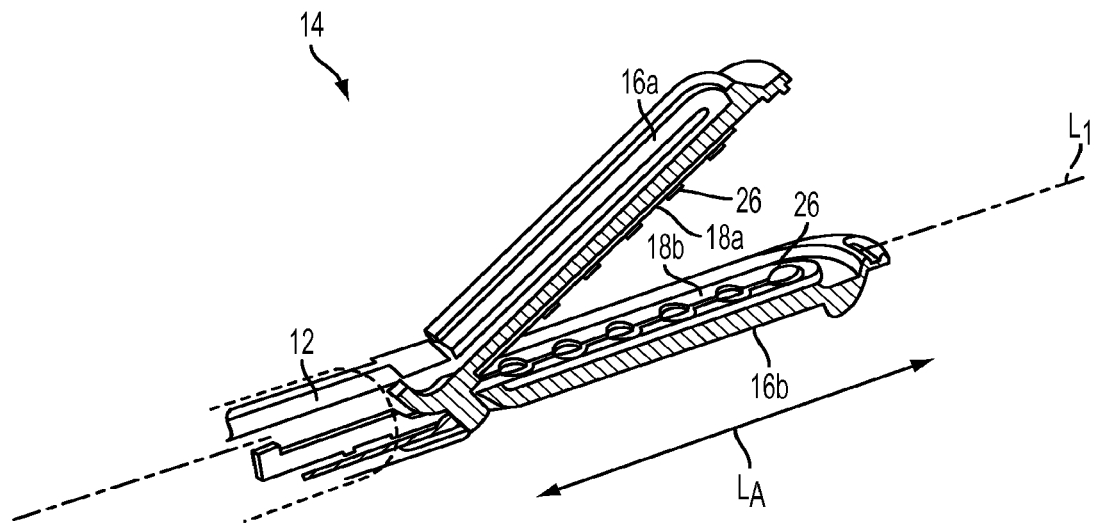
FIG. 2 is a perspective view of the end effector of FIG. 1 in an open position.
Figure 3:
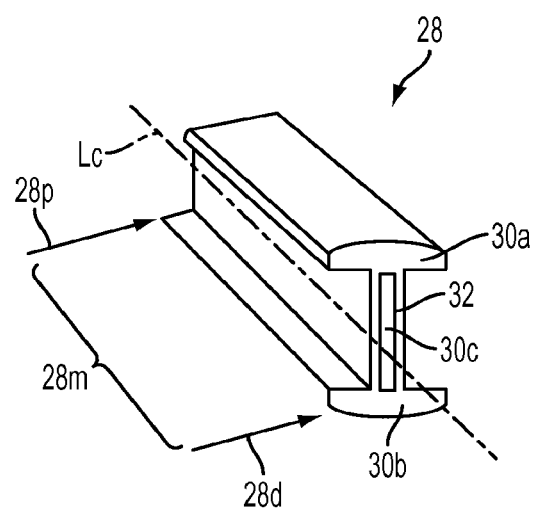
FIG. 3 is a perspective view of a compression member of the surgical device of FIG. 1.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Further, a person skilled in the art will recognize that a number of different terms can be used interchangeably while still being understood by the skilled person. By way of non-limiting example, the terms "cut" and "transect" are generally used interchangeably herein Still further, a person skilled in the art will recognize that the figures provided for herein are not necessarily to scale, and will recognize these figures that are close to or are to scale. For example, the compression member illustrated in FIG. 3 is not to scale in comparison to an end effector with which it can be used, illustrated in FIG. 2.

Surgical devices are provided herein having power-assisted jaw closure or fully-powered jaw closure to assist a user with manually closing the jaws, compressing tissue disposed between the jaws, and regulating an amount of compression applied by the jaws. In general, regulating compression applied by the jaws can promote healing and reduce damage to surrounding tissue. The devices herein generally include a handle portion, an elongate shaft, and an effector having first and second jaws configured to engage tissue therebetween. A motor and one or more compression springs can be operatively coupled together so that activation of the motor moves the springs between a compressed position and a relaxed position and causes the jaws to increase or decrease a force applied to tissue disposed therebetween. In some embodiments, the devices can apply energy in the form of electrical current to the tissue disposed in the jaws to seal the tissue. Sensors, processors, and/or other components can analyze tissue response to a given force, such as a cyclical compression force, and this data can be indicative of tissue type, tissue load, and/or another object such as a staple or clip being grasped by the device. In some embodiments, the device can automatically adjust parameters of the system, such as the amount of tissue compression or the amount of energy delivered to the tissue, based on the determined tissue type and/or tissue load.

Figure 1:
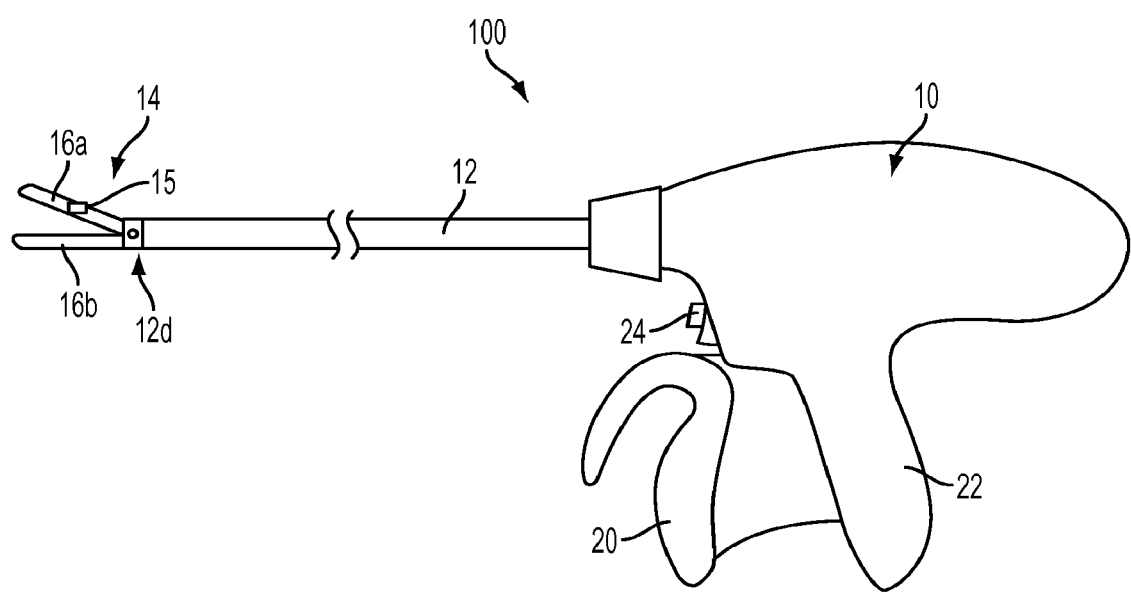
FIG. 1 is a side view of an exemplary embodiment of a surgical device having an end effector.

FIG. 1 illustrates one embodiment of a surgical device configured to grasp and cut tissue. A surgical device 100 can generally include a proximal handle portion 10, a shaft portion 12, and an end effector 14 for grasping tissue. The proximal handle portion 10 can be any type of pistol-grip or other type of handle known in the art that is configured to carry various actuators, such as actuator levers, triggers or sliders for actuating the end effector 14. In the illustrated embodiment, the proximal handle portion 10 includes a closure grip 20 and a stationary grip 22, and movement of the closure grip 20 toward and away from the stationary grip 22 adjusts a position of the end effector 14. The shaft portion 12 extends distally from the proximal handle portion and can have a bore (not shown) extending therethrough for carrying mechanisms for actuating the jaws.

The end effector can have a variety of sizes, shapes, and configurations. As shown in FIG. 1, the end effector 14 can include first and second jaws 16a, 16b disposed at a distal end 12d of the shaft portion 12. As can be seen in FIG. 2, the end effector 14 can include a first, upper jaw 16a and second, lower jaw 16b, one or both of which can be configured to close or approximate about an axis. Both of the jaws 16a, 16b can be movable relative to the shaft portion 12 or alternatively a single jaw can rotate so that the end effector 14 can move between a first, open position in which the jaws 16a, 16b are positioned at a distance apart to a second, closed position in which the jaws 16a, 16b are moved toward one another and are substantially opposed. When the jaws 16a, 16b are in the second, closed position, a longitudinal axis of the upper jaw 16a can be substantially parallel to a longitudinal axis of the lower jaw 16b and the jaws 16a, 16b can be in direct contact. In the illustrated embodiment, the upper jaw 16a can pivot relative to the shaft portion 12 and relative to the lower jaw 16b while the lower jaw 16b remains stationary.

Tissue disposed between the jaws can be compressed by the jaws when a threshold force is met or exceeded. More particularly, a user supplies a force to the jaws, for instance by way of closure grip 20, and when an amount of force supplied by the user exceeds the threshold force, the jaws can compress the tissue. Often times, this force is supplied prior to delivering energy to the tissue disposed between the jaws, for instance when the tissue is being sealed, in which case the force supplied to the tissue by the jaws may be referred to as a pre-compression force. The disclosures provided for herein reduce or decrease the threshold force. As a result, a user can supply less force to achieve the same compression output.

In the illustrated embodiment, the jaws 16a, 16b have a substantially elongate and straight shape, but a person skilled in the art will appreciate that one or both of the jaws 16a, 16b can be curved along axis $L_1$. The jaws 16a, 16b can have any suitable axial length $L_A$ for engaging tissue, where the axial length $L_A$ is measured along a longitudinal axis $L_1$ of the end effector 14, as shown in FIG. 2. The axial length $L_A$ of the jaws 16a, 16b can also be selected, at least in part based on the targeted anatomical structure for transection and/or sealing and the size, shape, and configuration of the other components of the device.

The jaws 16a, 16b can have any combination of features configured to facilitate grasping tissue therebetween. The first jaw 16a can have a first inner engagement surface 18a and the second jaw 16b can have a second inner engagement surface 18b, both of the first and second engagement surfaces 18a, 18b being configured to directly contact tissue. Either one or both of the engagement surfaces 18a, 18b can include one or more surface features formed thereon that can help secure the tissue thereon. For example, the surface features can include various teeth, ridges, or depressions configured to increase friction between the tissue and the engagement surfaces 18a, 18b of the jaws 16a, 16b without tearing or otherwise damaging the tissue in contact with such surface features. FIG. 2 illustrates a plurality of teeth 26 positioned along an axial length of both of the engagement surfaces 18a, 18b and can facilitate grasping tissue and forming substantially smooth, uniform layers of tissue to improve tissue effect. The first and second jaws 16a, 16b can optionally include features for interacting with a compression member (not shown) configured to apply compressive forces on the jaws 16a, 16b and tissue. For example, the first and second jaws 16a, 16b can include first and second recessed slots (not shown) that can receive portions of a compression member and act as a track to direct movement of the compression member. As the compression member is actuated distally along the axial length of the jaws 16a, 16b, the compression member can apply a force to one or both of the jaws 16a, 16b to approximate their inner engagement surfaces 18a, 18b closer together. Further, in some embodiments, the compression member can include a cutting edge that is effective to transect tissue disposed within the jaws 16a, 16b as the compression member is advanced distally.

A compression member can have various sizes, shapes, and configurations. In general, a compression member can have an elongate shape and can be movable proximally and distally along the longitudinal axis $L_1$ of the end effector 14. An exemplary compression member 28 is illustrated in FIG. 3. As shown, the compression member 28 can have a proximal end 28p, a medial portion 28m, and a distal end 28d. The proximal end 28p and the medial portion 28m of the compression member 28 can be sized and shaped to reciprocate within the shaft portion 12 of the device 100, while the distal end 28d of the compression member 28 can be sized and shaped to interact with the jaws 16a, 16b of the end effector 14. A longitudinal axis $L_C$ of the compression member 28 can be aligned and coaxial with longitudinal axis $L_1$ of the end effector 14 and of the shaft portion 12, though other configurations are possible.

The compression member 28 can be actuatable from the proximal handle portion of the instrument by any suitable mechanism that is operatively coupled to the proximal end 28p of the compression member 28, such as via the firing button 24 shown in FIG. 1. The compression member 28 can include a connecting portion 30c and upper and lower flanges 30a, 30b thus providing an "I-beam" type cross-sectional shape at the distal end 28d of the compression member 28. In the illustrated embodiment, the upper and lower flanges 30a, 30b are positioned substantially perpendicular to the connecting portion 30c to form the "I-beam" shape. As previously mentioned, the upper and lower flanges 30a, 30b can be sized and shaped to slide in the recessed slots in each of the upper and lower jaw 16a, 16b, and this sliding contact of lateral edges of the flanges 30a, 30b and sides of each of the recessed slot portions can prevent lateral flexing of the jaws 16a, 16b.

The compression member 28 can have various other configurations. For example, the upper flange 30a can have a width that is greater than a width of the lower flange 30b, the widths being measured in a direction perpendicular to the longitudinal axis $L_1$ of the end effector 14. The compression member 28 can vary in any number of ways and need not be limited to the illustrated embodiment. For example, the upper and lower flanges 30a, 30b can be disposed on the distal end 28d of the compression member 28 and need not extend from the proximal end 28p to the distal end 28d of the compression member 28.

The device can include a cutting member configured to transect tissue captured between the jaws, and the cutting member can vary in any number of ways. The cutting member can be sized and shaped to transect or cut various thicknesses and types of tissue positioned between the jaws of the end effector. In an exemplary embodiment, the cutting member is a cutting edge 32 positioned at the distal end 28d of the compression member 28, formed on the connecting portion 30c of the compression member 28. The cutting edge 32 can have a sharp or serrated edge configured to transect the tissue. In an exemplary embodiment, the cutting edge 32 can be recessed relative to distal ends of upper and lower flanges 30a, 30b of the I-beam compression member 28 so that compression occurs prior to transecting or cutting of the tissue. As will be appreciated by a person skilled in the art, in another embodiment the cutting member can be a knife blade that is not attached to a compression member such that the cutting member can advance and retract relative to the jaws without applying compression to the tissue.

Referring back to FIG. 1, the surgical device 100 can have a closure actuator 20 that can be configured to open and close the jaws 16a, 16b of the end effector 14. Manipulation of the closure actuator can pivot or otherwise move the jaws relative to one another such that the jaws can engage tissue, move anatomical structures, or perform other surgical functions. The closure actuator can have various sizes, shapes, and configurations, but in the illustrated embodiment the closure actuator includes the closure grip 20 and the stationary grip 22. The closure grip 20 can be movable toward and away from stationary grip 22, such as via pivoting. In particular, the closure grip 20 can have a first position in which it is angularly offset from the stationary grip 22 and the jaws 16a, 16b of the end effector 14 are open. The closure grip 20 can have a second position where it is positioned closer to the stationary grip 22, and may even be adjacent to or substantially in contact with the stationary grip 22. In this second position, the jaws 16a, 16b of the end effector 14 can engage tissue and apply a force to tissue disposed therebetween.

The closure grip 20 can be biased to the first open position with the jaws 16a, 16b of the end effector 14 being open, as shown in FIG. 1. The closure grip 20 can move the jaws 16a, 16b between the open and closed positions using manual or powered components. For example, in manually actuated embodiments, the pivotable arm 20 can be coupled to a gear that interacts with a rack extending in the handle and manual movement of the pivotable arm 20 toward the stationary grip 22 can move the rack distally toward the end effector 14, causing a force to be exerted onto the jaws 16a, 16b to close them.

In some embodiments, a motor can be disposed in the proximal handle portion 10 and manual movement of the pivotable arm 20 can cause a control signal to be sent to the motor, which causes the jaws 16a, 16b to close. The closure grip 20 can interact with one or more locking features (not shown) configured to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting. As will be appreciated by persons skilled in the art, in another embodiment a user can selectively actuate the locking feature to lock the closure grip at any desired angular position relative to the stationary grip.

As previously mentioned, in certain aspects the surgical device can have a second actuator that can be separate from the closure actuator. Actuator 24 can be configured to advance a cutting member, apply energy to tissue, or both, and is referred to herein as a "firing actuator." The firing actuator 24 can have various sizes, shapes, and configurations, but in illustrated embodiment can include a button or switch that can be depressed by a user. In another embodiment, the firing actuator 24 can include a trigger, switch, etc. that can be pivoted or otherwise moved by a user. Depressing or pivoting the actuator can activate various elements in the device, and can cause the cutting member to advance toward the end effector and/or cause energy to be delivered to the jaws, as will be discussed in greater detail below. For example, depressing or pivoting the firing actuator can cause the compression member and/or the cutting member to advance distally and/or retract proximally relative to the jaws 16a, 16b. More specifically, the firing actuator can be in electrical communication with a motor (not shown) disposed in the proximal handle portion 10. The motor can be operatively coupled to the compression member 28 using known components, such as a gear and rack. In this embodiment, activation of the motor can thus advance and/or retract the compression member 28. In some embodiments, the firing actuator 24 can be configured to close a circuit to deliver energy to an electrode disposed on surfaces of the jaws that engage tissue therebetween, as described elsewhere herein and as known to those having skill in the art.

Figure 4:
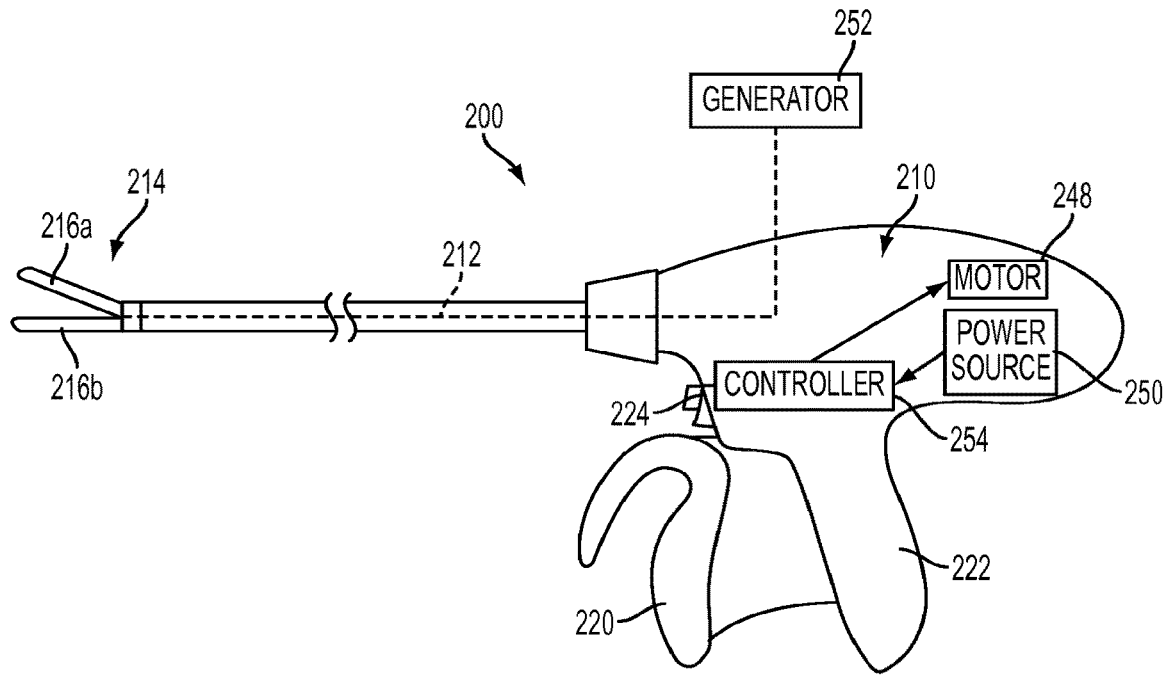
FIG. 4 is a schematic side view of an exemplary embodiment of a surgical device configured to apply energy to tissue.

Another embodiment of a surgical device is shown in FIG. 4. In this embodiment, the surgical device 200 can be configured to apply energy to tissue disposed between first and second jaws 216a, 216b. The surgical device 200 can include many of the features of the device 100 of FIG. 1, including first and second jaws 216a, 216b, a shaft portion 212, and a proximal handle portion 210. The surgical device 200 can include a compression member configured to cut tissue (not shown), a motor 248, a power source 250, a generator 252, and a controller 254. The device 200 can also include various components for generating energy and delivering such energy to tissue, for instance to seal the tissue, and these components can be disposed at various locations in the device 200, such as in the proximal handle portion 210 and/or in the jaws 216a, 216b, as will be explained in greater detail below. The surgical device 200 can include a generator that can be operatively coupled to the firing actuator 224 so that the device is configured to apply energy to tissue. The generator 252 can be any suitable generator known in the art, such as an RF generator. The generator 252 can be a separate unit that is electrically connected to the surgical device 200 to decrease a weight and size profile of the device 200. A bore (not shown) of the shaft portion 212 can carry electrical leads or wires that can deliver electrical energy to components of the end effector 214. As shown, the RF generator 252 can be coupled to the power source 250, such as a battery disposed in the proximal handle portion 210. While a number of devices and methods for grasping and sealing tissue are described below, others can be found, for example, in U.S. Ser. No. 14/149,279 entitled "Electrosurgical Sealing and Transecting Devices and Methods with Improved Application of Compressive Force," U.S. Pat. Pub. No. 2013/0161374, U.S. Pat. Pub. No. 2012/0083783, and U.S. Pat. Pub. No. 2004/0232197, which are incorporated by reference herein in their entireties.

Figure 5A:
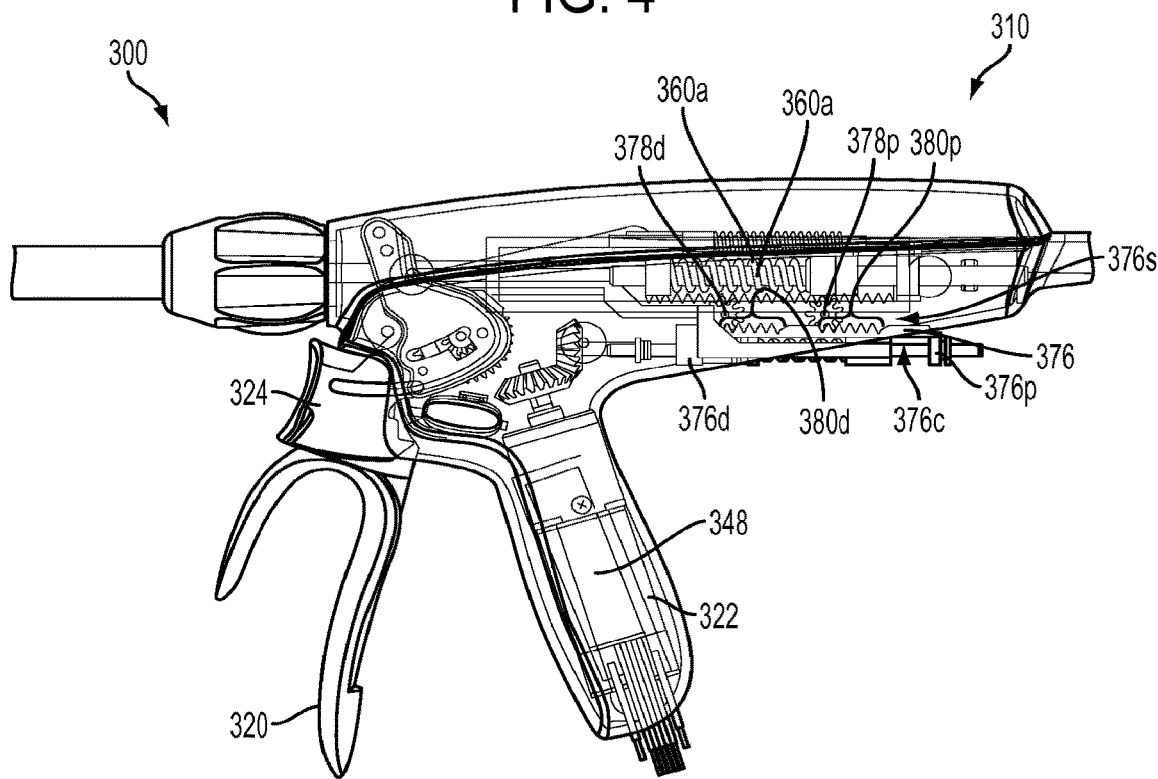
FIG. 5A is a partially transparent side view of an exemplary embodiment of a surgical device having a powered jaw closure system.
Figure 5B:
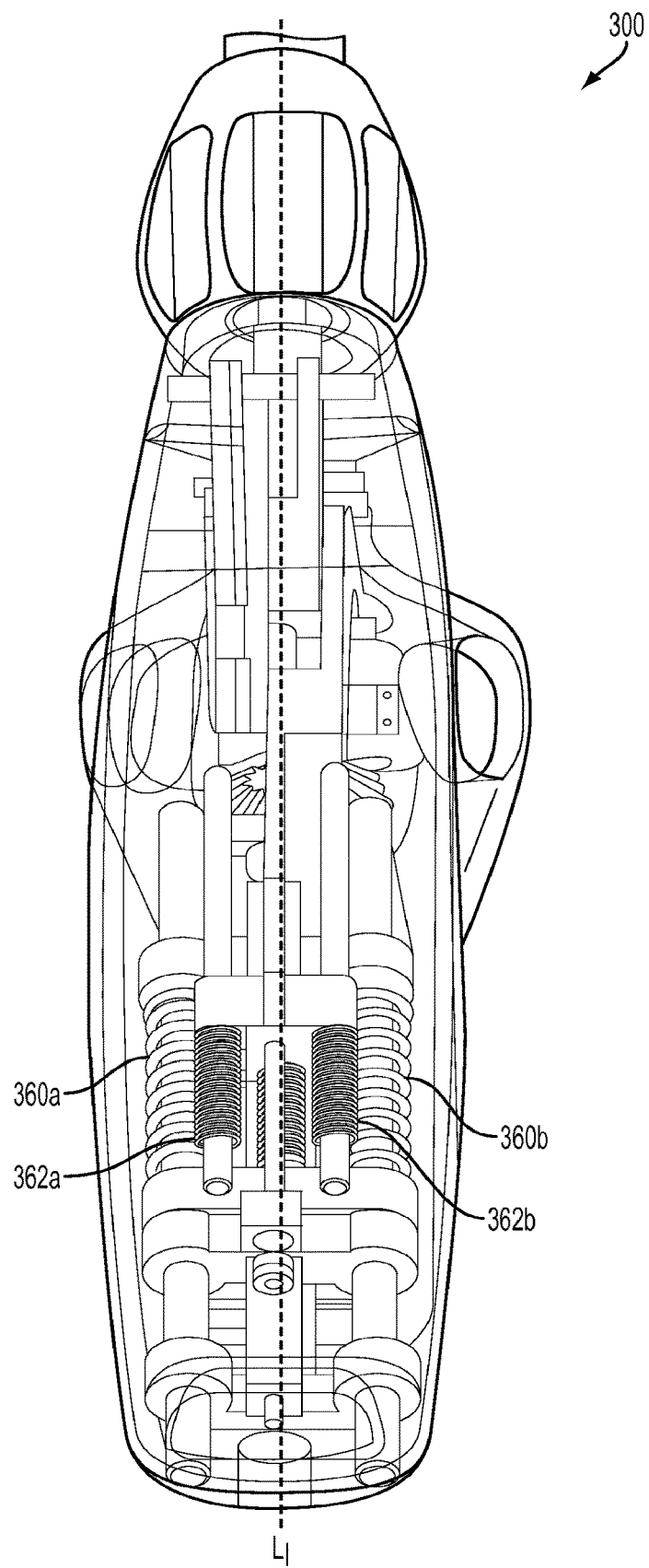
FIG. 5B is a partially transparent top view of the device of FIG. 5A illustrating compression springs and trigger return springs.
Figure 5C:
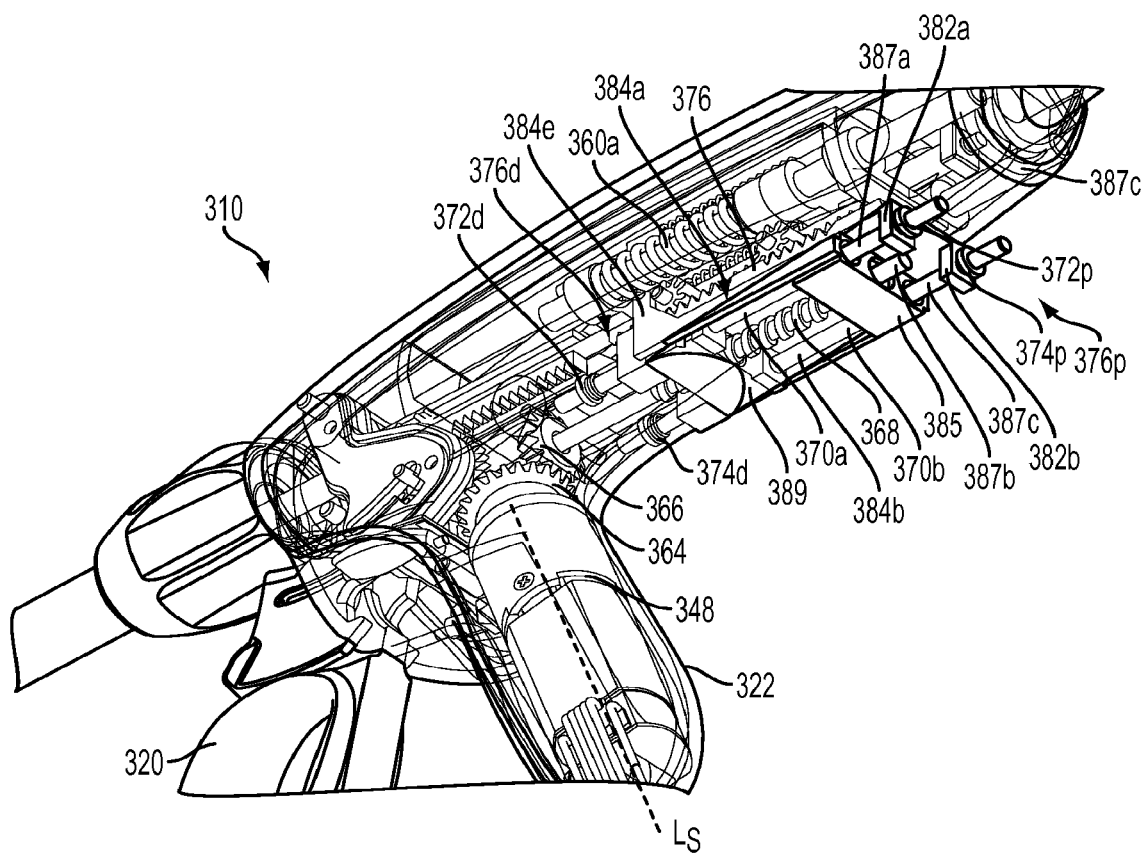
FIG. 5C is a partially transparent bottom perspective view of the device of FIG. 5A illustrating a driving member of the powered closure system.

A surgical device having power-assisted jaw closure is shown in FIGS. 5A-5C. As will be appreciated by those skilled in the art, the surgical device 300 can include any number of the features of devices 100, 200 previously described. As shown in FIG. 5A, the device 300 can include a housing 310 having a stationary grip 322, as well as closing and firing actuators 320, 324 that are movable toward the stationary grip 322. A motor 348 can be disposed in the stationary grip 322 and can be used for multiple functions. In the present instance, the motor 348 assists with compression of the jaws (not shown) onto tissue and advances a cutting member (not shown) to cut the tissue disposed in the jaws. The cutting member can be a compression member having a cutting edge, as previously described, or can be a separate knife blade.

One or more springs can be positioned in the housing and can assist the jaws with applying compression to tissue that is in addition to any compression applied from a user manually pivoting the closure actuator 320 toward the stationary handle 322. The force provided by the springs reduces the amount of force a user would otherwise need to supply to achieve the same pre-compression levels if the springs were not included. The housing 310 can include at least one power-biased compression spring 360a that can be operatively coupled to the motor such that activation of the motor 348 compresses the spring 360a. Similarly, the housing 310 can include at least one closure spring 362a that can be operatively coupled to the closure actuator 320. Activation of the closure actuator 320 can compress the closure spring 362a, as will be described in greater detail below. As shown in FIG. 5B, the device 300 includes first and second power-biased compression springs 360a, 360b that are laterally offset and on opposed sides of the longitudinal axis $L_1$ of the device 300, and first and second closure actuator return springs 362a, 362b that are laterally offset from and on opposed sides of the longitudinal axis $L_1$. The first and second closure actuator springs 362a, 362b can be disposed above the power-biased compression springs 360a, 360b, as shown, so as to minimize a size of the housing 310 and prevent interference between the springs 360, 362.

The motor 348 can be operatively coupled to the springs 360, 362 in various ways. For example, as shown in FIG. 5C, the motor 348 can include a shaft (not shown) having a first bevel gear 364 disposed thereon, a longitudinal axis of the shaft being aligned with a longitudinal axis Ls of the motor 348 and of the stationary grip 322. The first bevel gear 364 can mesh with a second bevel gear 366 disposed at an angle relative to the first bevel gear 364 to transfer rotation to a different location in the housing 310, the angle being in the range of about 45 to about 90 degrees, although other angles with respect to the motor and the gear, including an angle that is parallel to the shaft axis, are also possible. In the illustrated embodiment, for example, the first bevel gear 364 is positioned at an angle of about 60 degrees relative to the second bevel gear 366. Using the motors to compress the springs 360, 362 allows for pre-compression levels that would not otherwise by achievable by merely a manual application of force to the springs. The motor can supply enough force to compress the high-force precompression spring that are the springs 360a, 360b. Further, by relying on the reduced threshold force resulting from the motor compressing the springs 360a, 360b, the amount of mechanical advantage needed in the design of the device 300 is reduced in comparison to typical devices. This is particularly the case at the end of a trigger stroke, as the amount force felt needed for a user to overcome the resistance from tissue that builds up in the jaws is reduced by the springs 360a, 360b.

Various components can be used to translate rotation of the second bevel gear 366 into longitudinal translation that can compress one or more of the springs. As shown in FIG. 5C, the second bevel gear 366 can be coupled to a drive screw 368 that is substantially parallel to the longitudinal axis $L_1$ of the device. The drive screw 368 can be configured to transfer rotational movement of the bevel gear 366 into translation of one or more driving members, e.g., driving racks, coupled thereto. First and second rods 370a, 370b can help stabilize and support the driving members as they translate relative to the housing 310 and in certain aspects, can be disposed on opposite sides of the drive screw 368 in a fixed position relative to the housing 310. Each of the rods 370a, 370b can have one or more stops that can prevent the driving members from detaching from the rods 370a, 370b by sliding off of proximal and distal ends of the rods. For example, FIG. 5C illustrates the rods 370a, 370b having a proximal stop 372p, 374p and a distal stop 372d, 374d. The stops 372, 374 can have any size, shape, and configuration, but are shown as disc-shaped members. The stops 372, 374 can optionally include one or more dampening features, such as a spring. As will be appreciated, the dampening features can be disposed adjacent and just distal to the proximal stop and adjacent and just proximal to the distal stop to exert a biasing force in an opposite direction as the movement of the racks, such as to help bias driving members to their initial position prior to closure and/or firing of the device 300.

The driving members can have various sizes, shapes, and configurations. Referring back to FIG. 5A, a first driving member 376 can be configured to translate in a proximal-to-distal direction within the housing 310 in order to compress the one or more compression springs 362a, 362b. In general, the first driving member 376 can have proximal and distal ends 376p, 376d configured to mate with the first and second rods 370a, 370b, and a superior driving surface 376s for mating with one or more translation mechanisms, e.g., first and second pinions. The first driving member 376 can have an inferior surface 376i positioned directly above the first and second rods 370a, 370b and the drive screw 368, as shown.

The driving surface 376s can include various features, such as a proximal toothed portion 380p and a distal toothed portion 380d. In the illustrated embodiment, the proximal toothed portion 380p is configured to mate with a proximal pinion 378p and the distal toothed portion 380d is configured to mate with a distal pinion 378d. The proximal and distal ends 376p, 376d of the first driving member 376 can also have various configurations, but are generally configured to mate with at least one of the rods 370a, 370b and with the drive screw 368. For example, FIG. 5C illustrates the proximal end 376p of the first driving member 376 having first and second tabs 382a, 382b oriented substantially perpendicular to the superior driving surface 376s. The first and second tabs 382a, 382b can each include a hole or cutout formed therein that can be sized and shaped to receive one of the rods 370a, 370b therein. Similarly, the distal end 376d of the first driving member 376 can include one or more holes or cutouts (not shown) formed therein, each hole being sized and shaped to receive one of the rods 370a, 370b. The first driving member 376 can include at least one feature configured to directly mate with the threaded portion of the drive screw 368, such as a threaded hole (not shown) formed in the distal end 376d thereof.

As previously mentioned, the device can include a second driving member 384 configured to translate in a proximal-to-distal direction within the housing 310 in order to advance a cutting member relative to the jaws. The second driving member 384 can be a driving rack, as shown in FIG. 5C. In general, the second driving member 384 can be sized, shaped, and positioned on the rods 370a, 370b and drive screw 368 so as to not interfere with movement of the first driving member 376 and to allow the driving members 376, 384 to be independently movable. That is, the first driving member 376 can translate in the proximal-to-distal direction while the second driving member 384 remains axially fixed within the housing 310. Similar to the first driving member 376, the second driving member 384 can have various configurations, but is generally configured to mate with at least one of the rods 370a, 370b and the drive screw 368. As shown, the second driving member 384 can have a proximal end 384p that includes a support member 385 having a plurality of openings formed therein. The support member 385 can be a block having a substantially rectangular cross-sectional shape and can include three holes 387a, 387b, 387c formed therein, the first hole 387a for receiving the first rod 370a, the second hole 387b for receiving the second rod 370b, and the third hole 387c for receiving the drive screw 368. The holes 387a, 387b, 387c can be sized and shaped to allow the support member 385 to slide axially along the respective rod/screw. While a longitudinal length of the support member 385 can vary, the support member can have a longitudinal length that is less than a longitudinal length of each of the rods 370a, 370b and the screw 368 so as to minimize friction therebetween. For example, the longitudinal length of the support member 385 can be in the range of about 4 to about 40 millimeters. The device 300 can further include a support member 389 disposed at the distal end 384d of the second driving member 384, as shown.

The second driving member 384 can have various sizes, shapes, and configurations that can be operatively coupled to a cutting member (not shown) that cuts tissue in the jaws. In the illustrated embodiment, the second driving member 384 has substantially L-shaped lateral sides 384a, 384b, a distal end of each of the lateral sides 384a, 384b having an extension portion 384e that can be operatively coupled to a driving mechanism for advancing the cutting member relative to the jaws. While the extension portions 384e can have various configurations, in FIG. 5C they extend substantially perpendicular to the drive screw 368. The lateral sides 384a, 384b, can also include a central portion 384c positioned below and laterally offset from the inferior surface 376i of the first driving member 376, as shown. Proximal ends 384p of the lateral sides 384a, 384b can mate with and/or be integrally formed with the support member 385 that slides axially relative to the rods 370a, 370b and the drive screw 368.

Figure 6A:
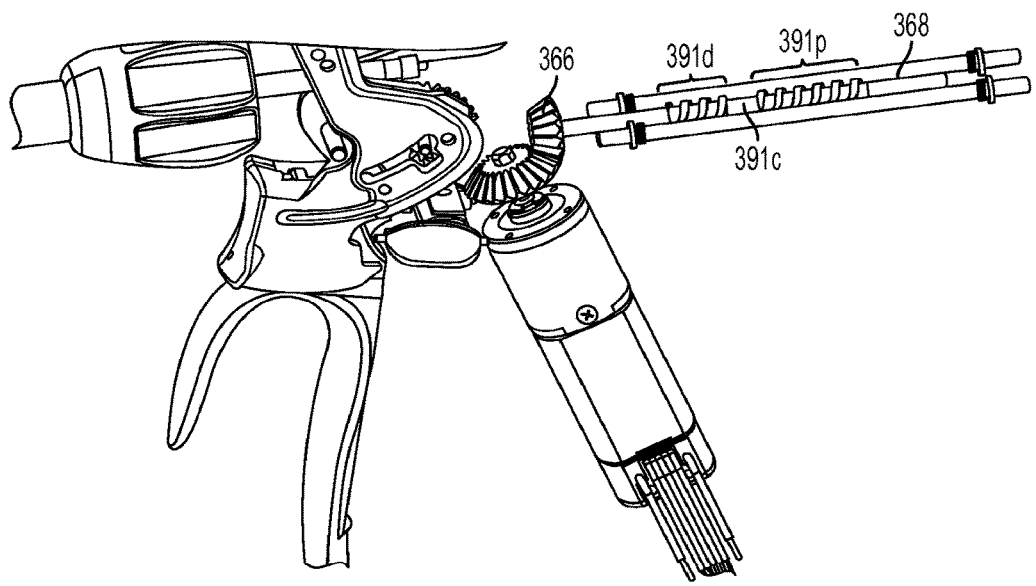
FIG. 6A is a side perspective view of a motor operatively coupled to a drive screw that effects closure of jaws of the end effector and advances a compression member within the jaws of the device of FIGS. 5A-5C.

FIG. 6A illustrates the drive screw 368 and first and second rods 370a, 370b in greater detail. As shown, the second bevel gear 366 can be coupled to a distal end of the drive screw 368. The drive screw 368 can have various features for mating with one or more driving members. For example, the drive screw 368 can include the proximal threaded portion 391p and the distal threaded portion 391d and a non-threaded portion 391c disposed in between. The proximal and distal threaded portions 391p, 391d can have various lengths, but in the illustrated embodiment the proximal threaded portion 391p is longer than the distal threaded portion 391d. In general, the length of the proximal threaded portion 391p is approximately equivalent to a length of the jaw, and the length of the distal threaded 391d corresponds to final travel required to fully compress the force-limiting spring. Therefore the proximal threaded length is typically longer than the length of the distal thread. As previously mentioned, the proximal threaded portion 391p can mate with the first driving member 376 and the distal threaded portion 391d can mate with the second driving member 384, such as via corresponding threads (not shown) formed on each of the driving members.

Figure 6B:
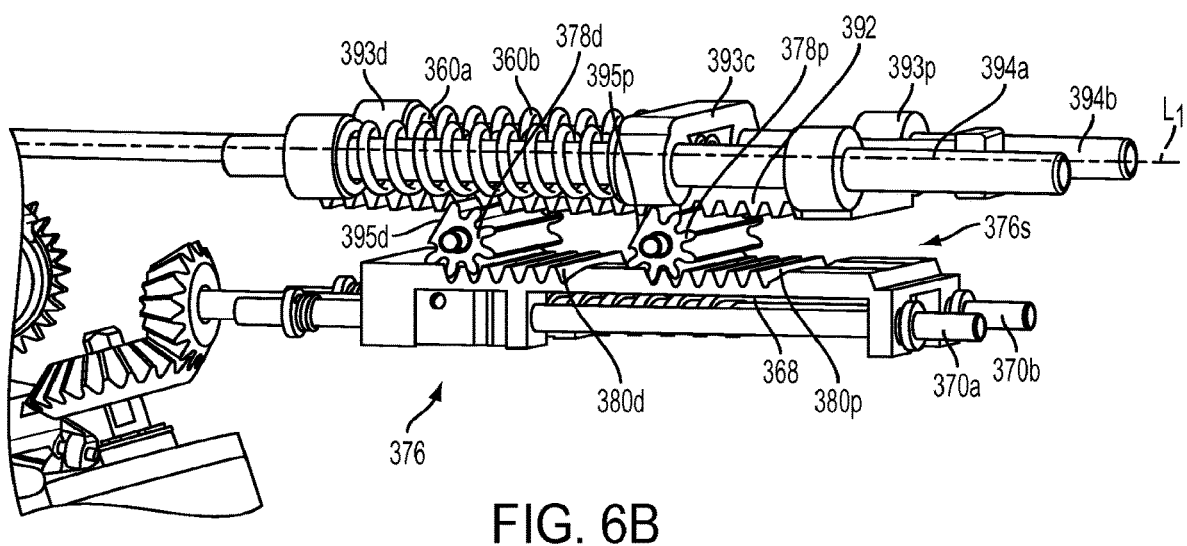
FIG. 6B is a side perspective view of drive mechanisms for compressing first and second compression springs of FIG. 5B.

FIG. 6B more clearly illustrates how the compression springs 360a, 360b are operatively coupled to the first driving member 376. As shown, the superior driving surface 376s of the first driving member 376 has a width perpendicular to the longitudinal axis that extends across a diameter of each of the first rod, the drive screw 368, and the second rod. The superior driving surface 376s can be coupled to one or more gears that can be used to reverse a translating force from distal-to-proximal to proximal-to-distal. For example, the first and second pinions 378p, 378d can be positioned above the superior driving surface 376s, as shown, and each pinion 378p, 378d can be coupled to a pin that is fixed within the housing 310. The first and second pinions 378p, 378d can have various sizes, shapes, and configurations. In the illustrated embodiment, the pinions 378p, 378d have a width that is substantially equal to the width of the superior surface 376s of the first driving member 376 and this can help stabilize the coupling between the pinions 378p, 378d and the toothed portions 380p, 380d of the superior driving surface 376s. However, the pinions 378p, 378d can have a width greater than or less than the width of the driving surface.

The first and second compression springs 360a, 360b can be positioned above the superior driving surface 376s and can include one or more features for mating with the pinions 378p, 378d. For example, a compression spring rack 392 can include a plurality of teeth directly coupled to the first and second pinions 378p, 378d. In certain aspects, the rack 392 can have a longitudinal length that can be substantially equal to or greater than the longitudinal length of the first and second rods and the drive screw 368. The rack 392 can be sized and shaped in various ways, but in the illustrated embodiment has a width that is substantially equal to the width of the pinions 378p, 378d, as this can help stabilize the coupling between the rack 392 and the pinions 378p, 378d.

The rack 392 can be configured to mate with first and second spring-holding rods 394a, 394b that are axially fixed within the housing 310 and are positioned laterally offset from and on opposite sides of the longitudinal axis $L_1$. The rack 392 can include one or more mating features, such as a proximal slider 393p and a distal slider 393d. In general, the proximal and distal sliders 393p, 393d can be fixedly coupled to and/or integrally formed with the rack 392 such that translation of the rack 392 also translates the sliders 393p, 393d axially within the housing. The sliders 393p, 393d can be shaped in various ways, but in the illustrated embodiment are in the form of two substantially cylindrical tabs positioned in a side-by-side relationship, each tab having a hole for receiving one of the spring-holding rods.

As shown, a central spring-support member 393c can be positioned at a location that is in between and spaced apart from both the proximal and distal sliders 393p, 393d. The central spring-support member 393c can include similar features as the proximal and distal sliders 393p, 393d, such as two substantially cylindrical tabs having holes for receiving one of the spring-holding rods. The first compression spring 360a can be positioned over the first spring-holding rod and the second compression spring 360b can be positioned over the second spring-holding rod, between the central spring-support member 393c and the distal slider 393d. The central spring-support member 393c need not be coupled to the rack 392 and can be axially fixed within the housing so that proximal translation of the distal slider 393d can compress the compression springs 360a, 360b against the central spring-support member 393c.

The teeth formed on the driving rack 376, the compression spring rack 392, and the pinions 378p, 378d can be selected to produce a desired amount of compression of the first and second compression springs. In general, the first and second pinions 378p, 378d can have any number of teeth that can mate with the toothed portion of the rack 376p, 376d and a toothed portion of the compression spring rack 392. Each of the pinions 378p, 378d can further include a flat portion 395p, 395d along a circumference thereof that can prevent the rack 392 from advancing any further, thereby maintaining the precompression springs 360a, 360b at a desired location. For example, the pinions 378p, 378d can have any number of teeth in the range of about 4 to about 40. The proximal and distal toothed portions 380p, 380d of the driving rack 376 can have a number of teeth that corresponds to (i.e., is substantially equal to) the number of teeth on the pinions 378p, 378d, in the range of about 2 to about 40. The flat portions 395p, 395s are positioned such that as driving rack 376 is advanced distally the flat portions 395p and 395s contact the flat surfaces on driving rack 376 thereby acting as a brake by preventing the compression forces in spring 360a, 360b from back driving or reversing the rotation of pinions 378p, 378d. This insures that compression springs 360a, 360b maintain their force as drive screw 368 continues to rotate to advance second driving member 384 and the corresponding cutting member (not shown).

Figure 7A:
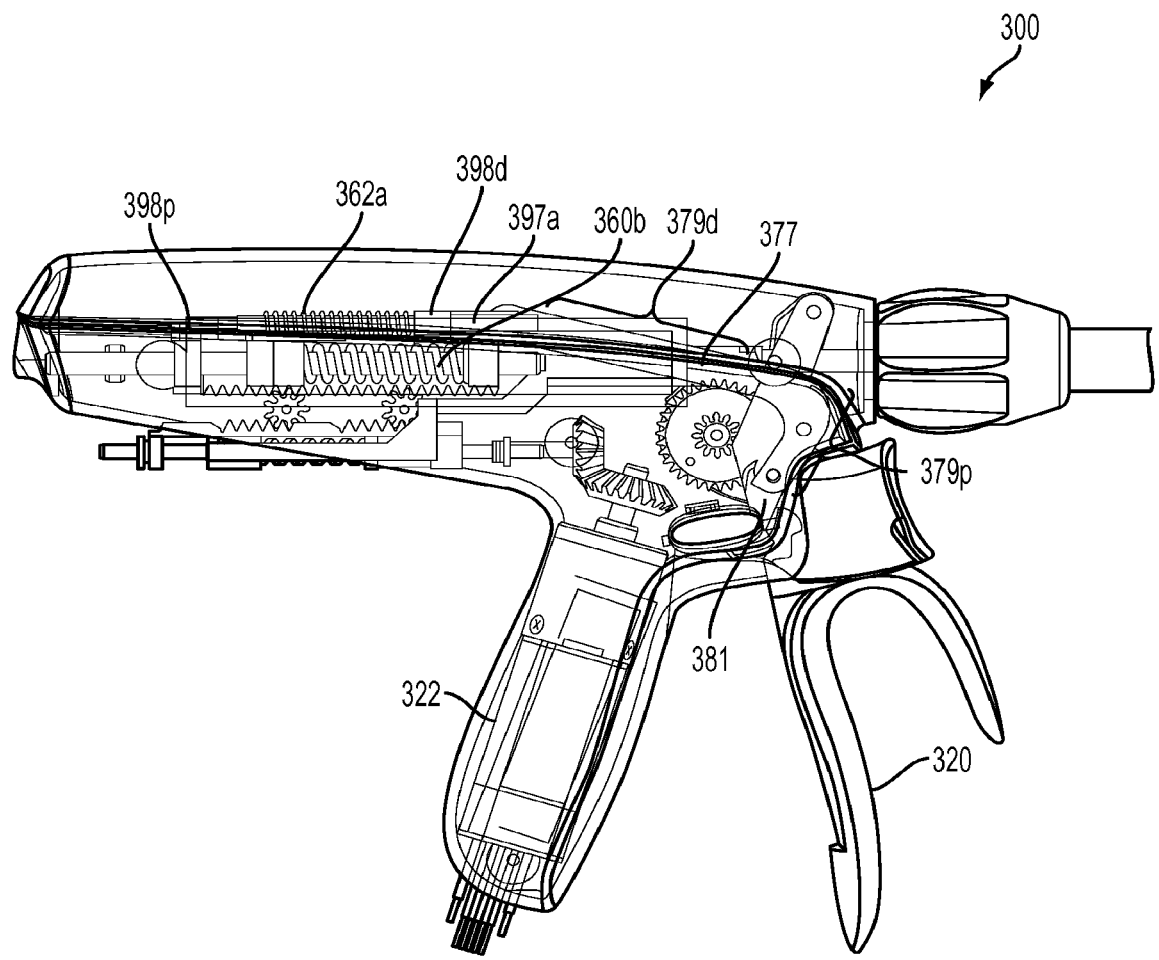
FIG. 7A is a partially transparent side view of the device of FIGS. 5A-5C illustrating the trigger return spring in a first, resting position, a closure actuator being positioned away from a stationary handle.
Figure 7B:
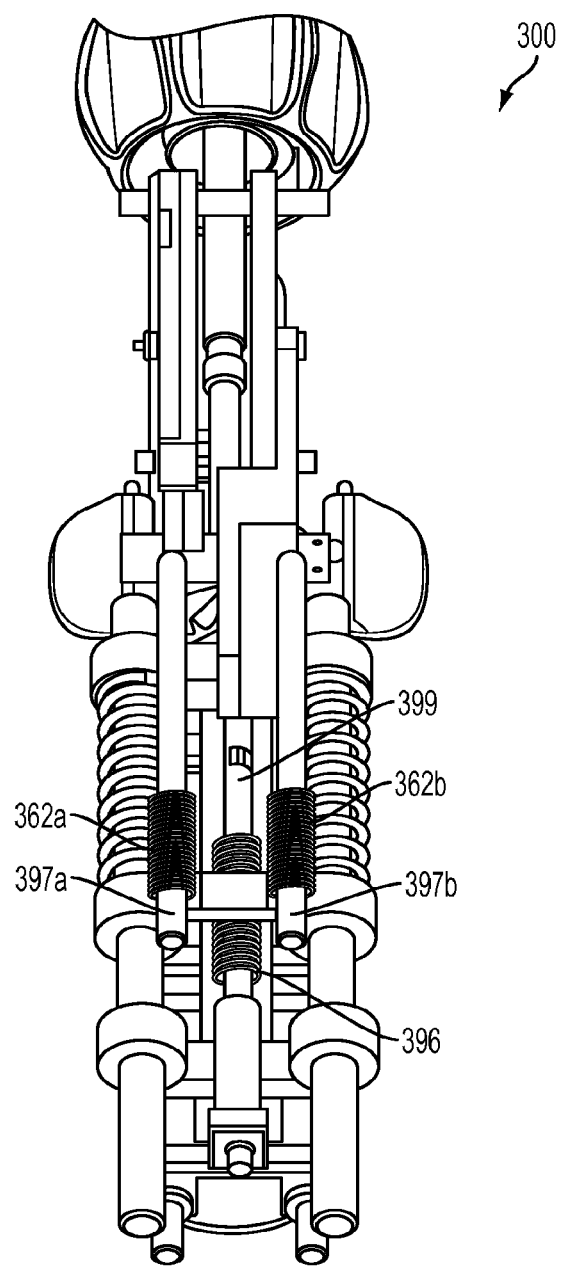
FIG. 7B is a top view of a manual compression spring of the device of FIGS. 5A-5C disposed in a compressed position with a housing removed for illustrative purposes.
Figure 7C:
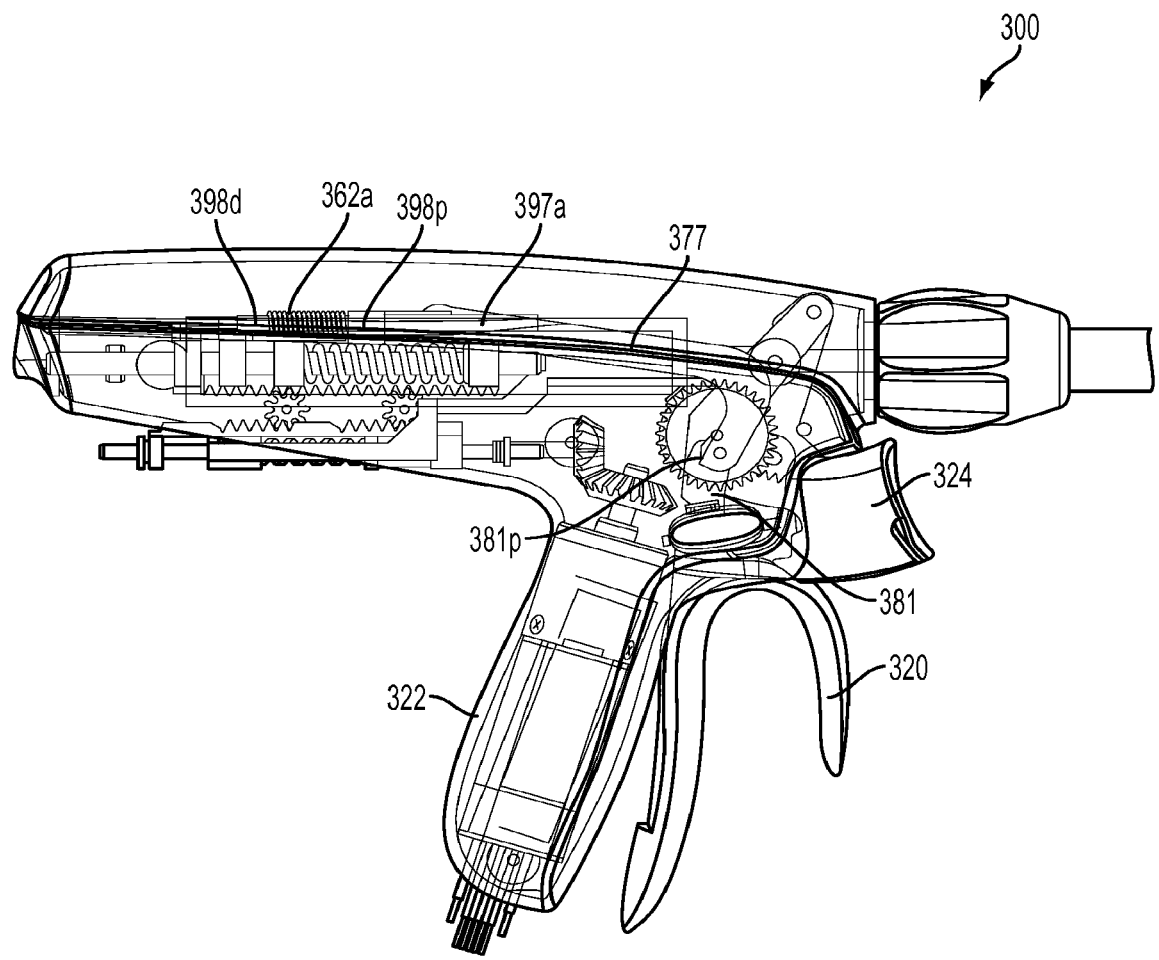
FIG. 7C is a partially transparent side view of the device of FIGS. 5A-5C illustrating the closure actuator in a position adjacent to the stationary handle and the trigger return spring in a second, compressed position.

FIGS. 7A-7C illustrate a manual jaw compression system of the device 300, which utilizes the manually driven closure actuator 320 to compress a manual compression spring 396. This system can apply additional compression to tissue disposed between the jaws and at the same time, can give a user tactile feedback as to tissue type and/or thickness based on the resistance to compression. As shown, the device 300 includes at least one trigger return spring 362 positioned above the first and second powered compression springs 360a, 360b. In the illustrated embodiment, the device 300 includes the first trigger return spring 362b and the second trigger return spring 362a, each spring being disposed around a rod 397a, 397b that extends substantially parallel to the longitudinal axis of the device 300. Each of the trigger return springs 362a, 362b can be disposed in between a proximal spring-support member 398p and a distal slider 398d, the spring-support member 398p being axially fixed within the housing 310 and the distal slider 398d being movable toward the proximal-spring support member 398p to compress the trigger return spring(s) 362a, 362b.

The manual jaw compression system can further include a central rod 399 disposed in between the first and second rods 397a, 397b, as shown in FIG. 7B. The central rod 399 can be operatively coupled with the jaws such that when the manual compression spring 396 disposed on the central rod 399 is compressed, the jaws are pivoted closed and apply an additional compression force to tissue disposed therein. Moving in a proximal-to-distal direction, the distal slider 398d can be coupled to a pivotable arm 377 that transfers pivotable movement of the closure actuator 320 into translation of the distal slider 398d and thus, compression of the trigger return springs 362a, 362b. The distal slider 398d can include various features for coupling to a proximal end 377p of the pivotable arm 377, such as first and second extension arms (not shown) extending distally therefrom for receiving the proximal end 377p of the arm 377 therebetween. For example, the first and second extension arms can include holes that can receive a pin that extends through a corresponding hole formed in the arm to fix the extension portions to the proximal end 377p of the arm 377. While the pivotable arm 377 can be shaped in various ways, in the illustrated embodiment the arm 377 is substantially L-shaped, including a first elongate portion 379d and a second elongate portion 379p that is substantially perpendicular to the first elongate portion 379d. A linkage bar 381 can be coupled to and extend between the first elongate portion 379d and the closure actuator 320, as shown in FIG. 7A. When the closure actuator 320 is pivoted toward the stationary handle 322, as in FIG. 7C, the linkage bar 381 and thus, the pivotable arm 377 are moved proximally. In this way, a proximal end 381p of the linkage bar 381 also moves proximally and causes the distal slider 398d to translate proximally to compress the trigger return springs 362a, 362b.

The compression springs, trigger return springs, and manual compression spring can have various sizes and can be formed from various material selected so that the spring has a desired spring constant. The selection of sizes and materials can depend, at least in part, on the sizes and materials of the other components involved in compressing tissue. In some exemplary embodiments, the springs can be made from 302 stainless steel or 17-7 precipitation hardened stainless steel, the springs can have a length in a neutral position (i.e., neither compressed nor expanded) approximately in the range of about 2 millimeters to about 250 millimeters. Trigger return springs 362a, 362b can be designed with the least force and the powered compression springs 360a, 360b can be designed to generate the most force of the three sets of springs. As a result, the amount of force applied to the closure actuator 320 to manually compress tissue in the jaws is reduced in the range of about 10 to 80%.

FIGS. 8A-8D illustrate the surgical device 300 of FIGS. 5A-5C, the device 300 being shown in various positions prior to and following activation of a closure actuator 320, and following activation of a firing actuator 324. Like many of the illustrations provided herein, housing 310 of the device 300 is depicted as a transparent feature so that the position of the driving members and compression springs are visible.

Figure 8A:
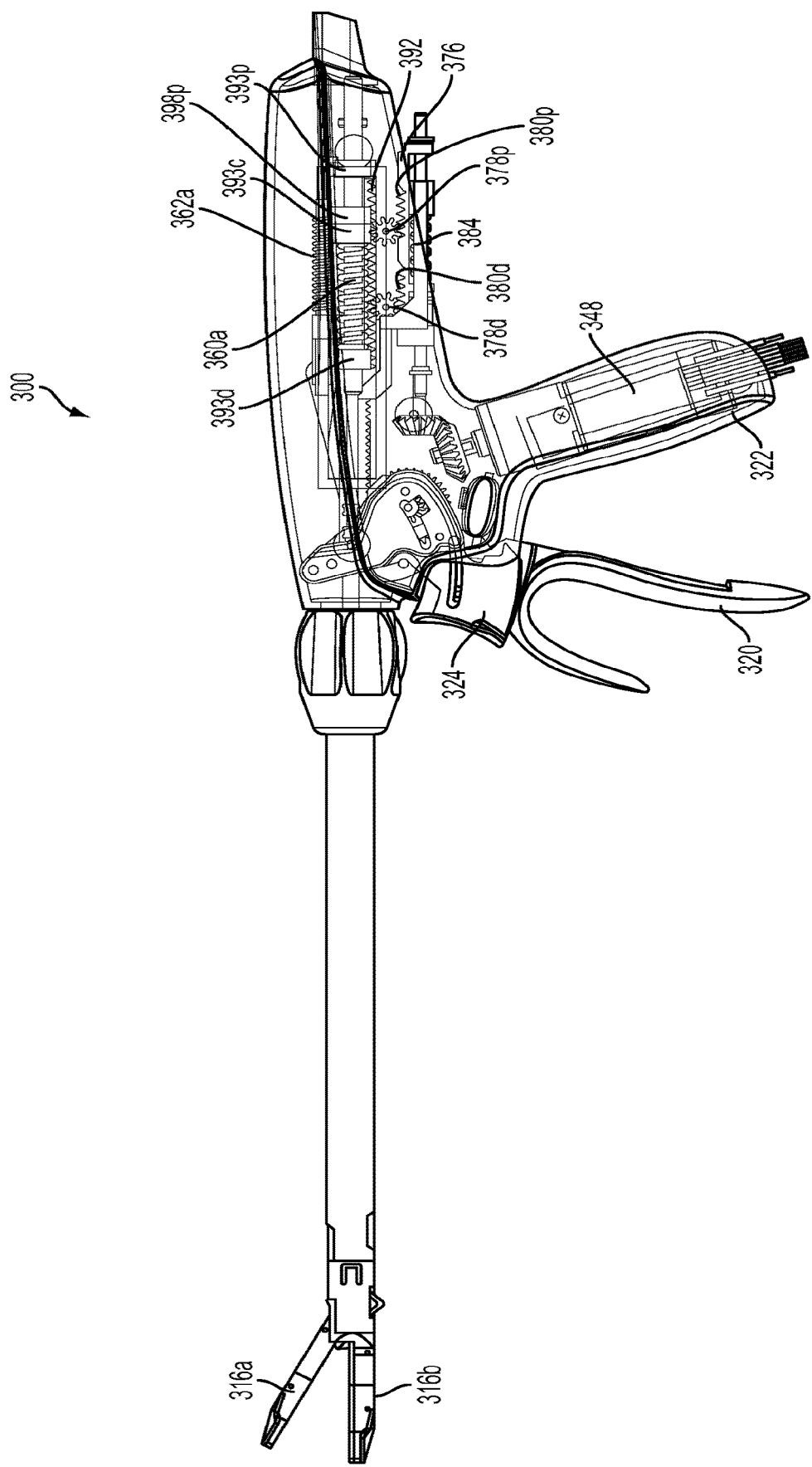
FIG. 8A is a partially transparent side view of the surgical device of FIGS. 5A-5C in a first position where jaws of an end effector are open and the compression and trigger return springs are in a first, resting position.

FIG. 8A is a side view of the device 300 in a first position where the jaws 316a, 316b are open and the compression and trigger return springs 360a, 360b, 362a, 362b are in a first, resting position. In this position, the closure actuator 320 and firing actuator 324 are inactive because the closure actuator 320 is disposed at a distance away from the stationary handle 322 with no manual force being applied thereto. As a result, the motor 348 in the stationary handle 322 is also inactive and the first and second jaws 316a, 316b are spaced apart. With the jaws 316a, 316b and actuators 320, 324 so positioned, the power-biased compression springs 360a, 360b, trigger return springs 362a, 362b, and manual compression springs 396 can each be in a first, resting configuration where there is no compression force being applied thereto. The toothed portions 380p, 380d of the first driving member 376 can be in mesh with the first and second pinions 378p, 378d. That is, the proximal pinion 378p can be positioned at a distal end of the proximal toothed portion 380p and the distal pinion 378d can be positioned at a distal end of the distal toothed portion 380d. A superior surface of each of the pinions 378p, 378d can be in mesh with the inferior surface 392i of the rack 392. The first and second driving members 376, 384 are in their proximal-most positions in preparation for distal translation relative to the housing 310. The proximal slider 398p of the trigger-return spring 362a is positioned adjacent to the central support member 393c of the compression springs 360a, 360b, as shown.

Figure 8B:
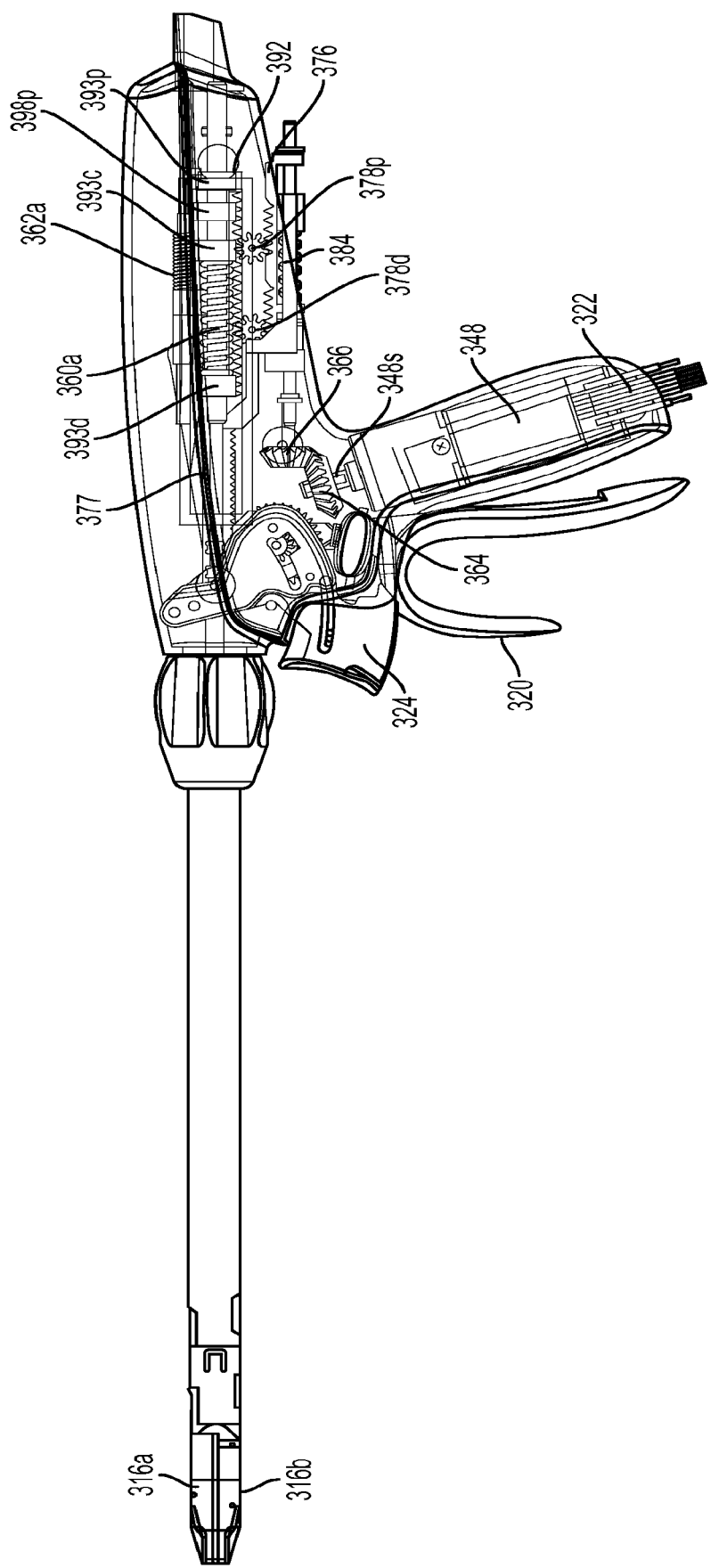
FIG. 8B is a partially transparent side view of the device of FIG. 8A where the jaws are closed and the trigger return spring is in a second, compressed position.

FIG. 8B is a side view of the device when the closure actuator 320 is positioned adjacent to the stationary handle 322 such that the jaws 316a, 316b are closed and the trigger return springs 362a, 362b and the manual compression spring (not shown) are in a second, compressed position. With the actuator 320 so positioned, the motor 348 is activated, which rotates its drive shaft 348s, the first bevel gear 364, and then the second bevel gear 366. This causes the drive screw 368 to rotate within the housing 310 and starts translation of the first driving member 376 in a proximal direction. The proximal slider 398p of the trigger-return spring 360a has translated proximally relative to the central support member 393c due to the compression force applied to the trigger-return spring 362a via the pivotable arm 377.

Figure 8C:
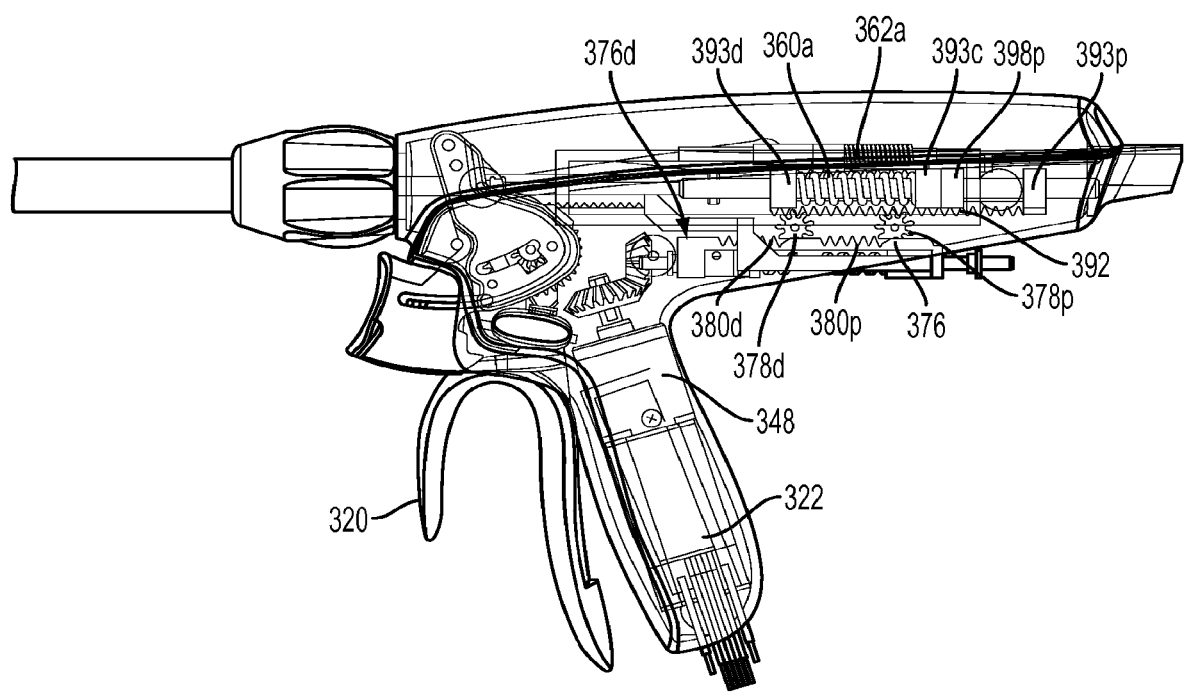
FIG. 8C is a partially transparent side view of the device of FIG. 8A after the motor has been activated and the compression spring has moved to a second, compressed position.

FIG. 8C is a side view of the device 300 after the motor 348 is activated and the compression spring 360a has moved to a second, compressed position. As shown, the first driving member 376 has been translated distally via rotation of the drive screw 368 such that the distal end 376d of the first driving member 376 abuts the distal stop of each of the first and second rods (not shown). Distal translation of the first driving member 376 causes the pinions 378p, 378d to rotate in a clockwise direction until flat portions 395p, 395d of each of the pinions 378p, 378d thereof can prevent the rack 392 from advancing any further, thereby maintaining the precompression springs 360a, 360b at the desired location, as described in greater detail elsewhere herein. Rotation of the pinions moves the distal slider of the rack proximally, compressing the first and second compression springs, as in FIG. 8C. The manual compression spring remains compressed, as mentioned above, or it slightly decompresses if compression of the powered compression springs move the proximal spring-support member 398 proximally. With the compression springs 360a, 360b and trigger return springs 362a, 362b compressed, the central support member 393c can once again be positioned adjacent to the proximal slider of the trigger return spring 362a and the first and second pinions 378p, 378d can be positioned at a proximal end of the toothed portions 380p, 380d. With the pinions 378p, 378d in the locked position, continued rotation of the drive screw 368 advances the second drive member 384 distally while the first drive member 376 remains axially fixed within the housing 310. By moving the compression spring 360a to the second, compressed position, a large force can then be transmitted to the jaw closure mechanism to enable additional compression of the tissue in the jaws of the device via motor activation.

Figure 8D:
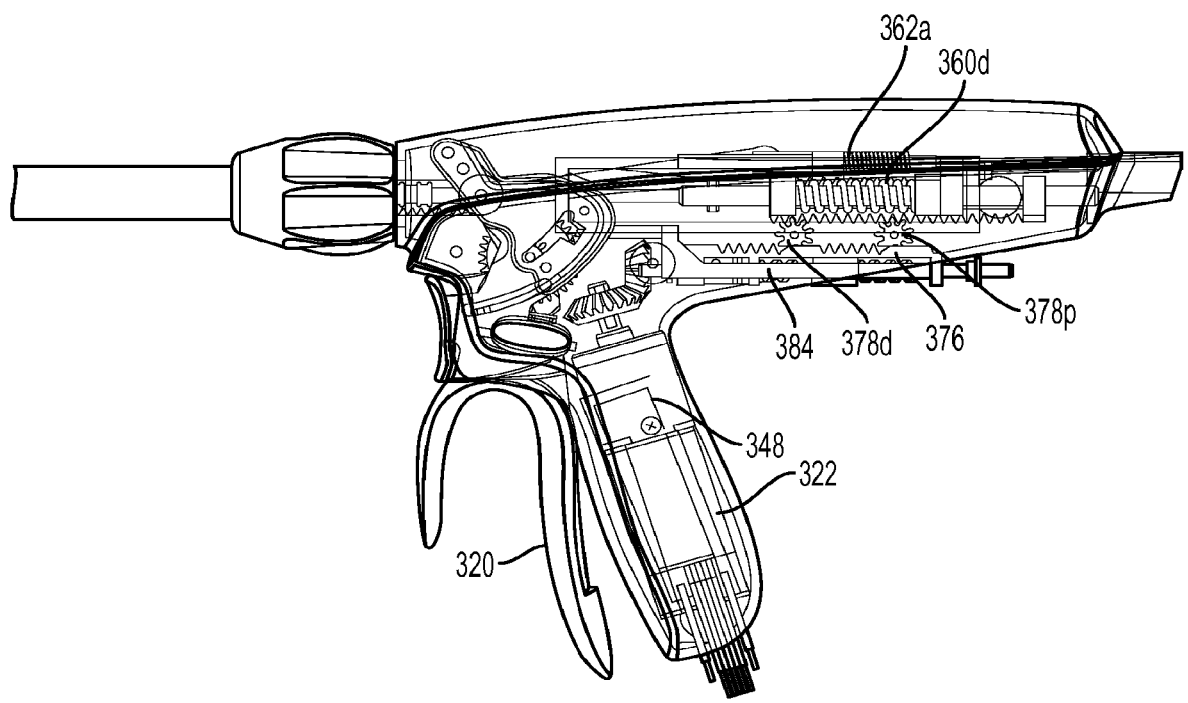
FIG. 8D is a partially transparent side view of the device of FIG. 8A after the driving member has moved distally to advance the compression member relative to the jaws.

FIG. 8D is a side view of the device 300 after the motor 348 has moved the second drive member 384 to its distal-most position. As previously mentioned, because the second drive member 384 is operatively coupled to the cutting member (not shown), distal movement of the second drive member 384 can advance the cutting member relative to the jaws 316a, 316b to cut tissue disposed therein. Accordingly, the motor 348 drives movement of both the manual compression spring and advancement of the cutting member.

The surgical devices can include various combinations of the features described above and, for example, need not include the first driving member and the pinions. A person skilled in the art will recognize a variety of other mechanical and actuating components that can be used to compress the springs in the housing. In some embodiments, a surgical device can include a second driving member for advancing the cutting member relative to the jaws and the driving screw can have a single threaded portion rather than two threaded portions. A jaw closure cam can be operatively coupled to the jaws such that as the drive screw is rotated by the motor, the jaw closure cam can move distally and cause the jaws to close.

In another embodiment (not shown), a surgical device can have fully automated, powered jaw closure. More specifically, the surgical device need not include a mechanical linkage between the closure actuator and the jaw, and instead can be configured so that an angular position of the closure actuator relative to the stationary handle produces a corresponding angular position of the jaws. For example, an angular encoder can translate an angular position of the closure actuator relative to the stationary handle to the jaws so that the jaws have a corresponding angular position. Because closure and compression of the jaws is accomplished using a motor rather than manually actuated components, the total compression force applied to the jaw can be as high as needed, while a force felt by a user as the user moves the closure actuator can be as low as desired.

Figure 9A:
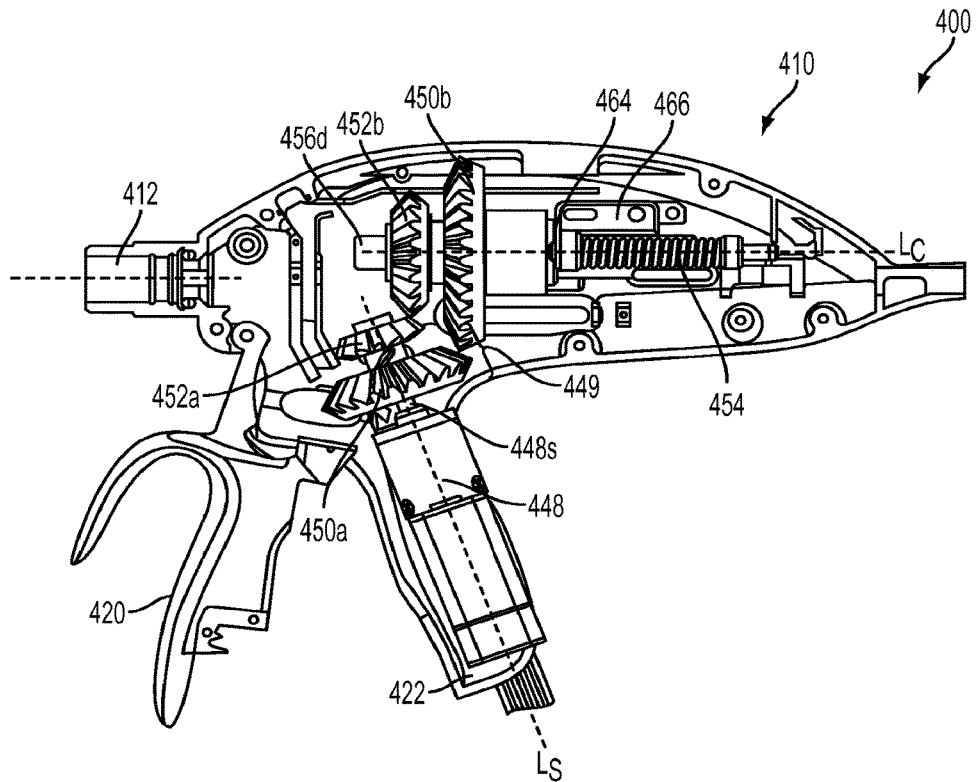
FIG. 9A is a partially transparent side view of another exemplary embodiment of a surgical device having a first set of gears for compressing a compression spring and a second set of gears for advancing a compression member relative to jaws of an end effector (not shown)
Figure 9B:
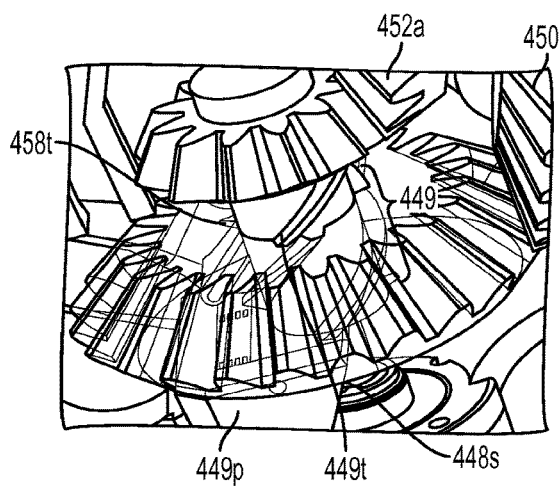
FIG. 9B is a partially transparent perspective view of a closure gear of the device of FIG. 9A that is axially movable relative to a compression member gear via a bendix.
Figure 9C:
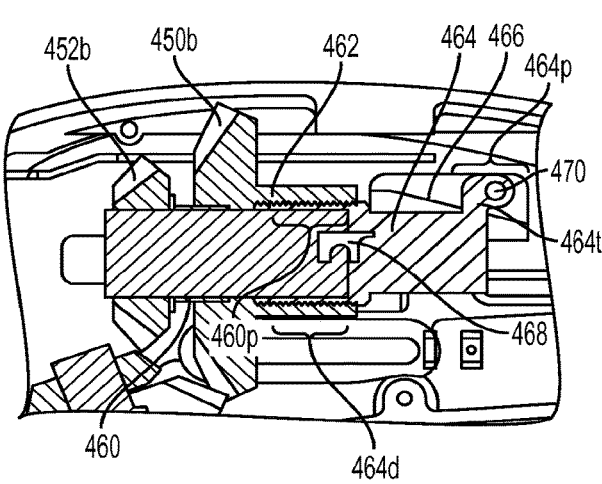
FIG. 9C is a side cross-sectional view of the of the device of FIG. 9A illustrating a mating connection between a closure gear, a sliding member, and the compression spring.

FIGS. 9A-9C illustrate a surgical device 400 having fully automated, powered jaw closure rather than power-assisted jaw closure. A housing 410 of the surgical device 400 is shown in FIG. 9A and can include various components previously described, such as a closure actuator 420, motor 448, shaft 448s, and one or more compression springs 454, as shown. The device 400 can include a spring-loaded bendix mechanism 449 that is configured to move a first compression gear 450a and first blade advancing gear 452a away from the motor 448 when the motor 448 is activated. The bendix mechanism 449 can also be configured so that the compression gear 450a can remain stationary while the blade advancing gear 452a is rotated, depending on how long the motor 448 has been activated and on the position of the bendix 449. The bendix 449 can allow for selective application of compression to the jaws before advancement of a cutting member within the jaws to cut tissue disposed therein.

In the illustrated embodiment, the device 400 includes a single compression spring 454 that has a longitudinal axis $L_C$ aligned with the longitudinal axis $L_1$ of the shaft 412. The housing 410 can include a plurality of gears that transfer rotation of the drive shaft 448s of the motor 448 to various other components to close the jaws and/or so that the jaws apply compression to tissue disposed therein. For example, the device 400 can include the first compression gear 450a and the first blade advancing gear 452a spaced axially apart, as in FIG. 9A. The compression gear 450a can be positioned closest to the motor 448, while the blade advancing gear 452a can be positioned further away from the motor 448 than the compression gear 450a. The compression gear 450a and the blade advancing gear 452a can rotate about a longitudinal axis Ls extending through the motor 448 and the stationary handle 422. An opening can be formed in the first compression gear 450a and can have corresponding indentations 458t formed on an inner surface thereof, as shown in FIG. 9B, so that the bendix mechanism 449 can rotate the first compression gear 450a when threads 449t of the bendix mechanism 449 are in contact with the indentations 458t.

Referring back to FIG. 9A, the device 400 can further include a second compression gear 450b and a second blade advancing gear 452b, and the gears 450b, 452b can be positioned above both the first compression gear 450a and the first blade advancing gear 452a, as shown. The second compression gear 450b and the second blade advancing gear 452b can rotate about the longitudinal axis $L_C$, as shown. As will be appreciated, the second blade advancing gear 452b can be operatively coupled to a cutting member (not shown) via a mating feature 456d disposed on a distal end thereof such that rotation of the gear 452b causes the cutting member to advance distally and/or proximally within the jaws. The first compression gear 450a can mesh with the second compression gear 450b, which can be disposed at an angle in the range of about 70 degrees to about 130 degrees relative to the first compression gear 450a, and in one exemplary embodiment the angle is about 110 degrees. Similarly, the first blade advancing gear 452a can mesh with the second blade advancing gear 452b, which can be disposed approximately at the same angle as the angle between the first and second compression gears 450a, 450b.

The second compression gear and the second blade advancing gear 450b, 452b can each include a shaft 460, 462 that extends proximally therefrom for mating with other components, such as a coupler 464 shown in FIG. 9C. While the shafts 460, 462 can be shaped in various ways, in the illustrated embodiment the shafts 460, 462 have a substantially cylindrical shape and the gears 450b, 452b are mounted on a distal end thereof. The shaft 460 of the blade advancing gear 452b can be a substantially solid member to provide additional support to the gears 450b, 452b. The shaft 462 of the second compression gear 452b can have an opening extending between the proximal and distal ends sized and shaped so that the shaft 460 of the blade advancing gear 452b can be received therein. The coupler 464 can have first and second ends 464p, 464d, the first end 464d for holding a proximal end 460p of the shaft 460 of the second blade advancing gear 452b therein and a second end 464p for mating with a slidable member 466 that translates axially to compress the compression spring 454. As shown, the coupler 464 can have a recess formed therein that is sized and shaped to correspond with a size and shape of the proximal end 460p of the shaft 460, such as a recess having a substantially cylindrical shape. The coupler 464 can mate with the compression gear shaft 462 in various ways. For example, an outer surface of the first, distal end 464d of the coupler 464 can have threads formed thereon that mate with corresponding threads formed on an inner surface of the opening in the compression gear shaft 462.

The second, proximal end of the coupler 464p can have a diameter that is smaller than a diameter of the first, distal end 464d as shown, or the diameter of the coupler 464 can be substantially constant along its length. The coupler 464 can be configured to mate with the slidable member 466 which can translate axially within the housing 410 to compress the compression spring 454. As shown, the coupler 464 can include a tab 464t formed on the proximal end 464p thereof that can receive a pin 470 therethrough that extends into the slidable member 466 to complete the mating connection. A distal end of the slidable member 466 can in turn be coupled to a distal end of the compression spring 454, while a proximal end of the compression spring 454 can be fixed to the housing 410 such that proximal movement of the slidable member compresses the compression spring 454.

Figure 10A:
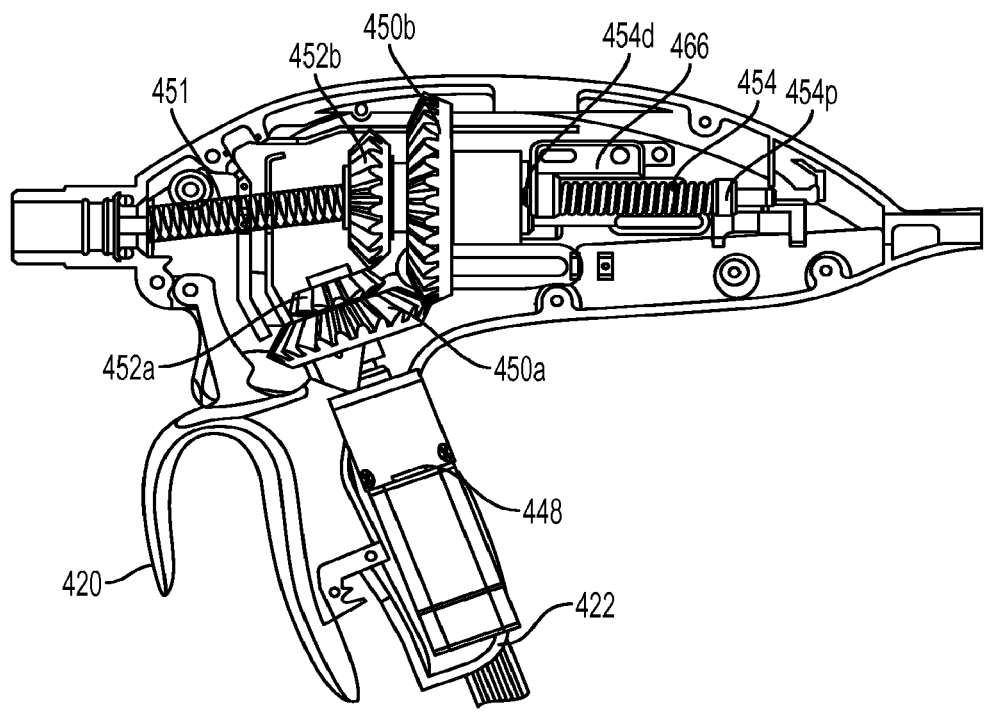
FIG. 10A is a partially transparent side view of the device of FIG. 9A after a motor has been activated and a closure gear has translated away from the motor to compress the compression spring.
Figure 10B:
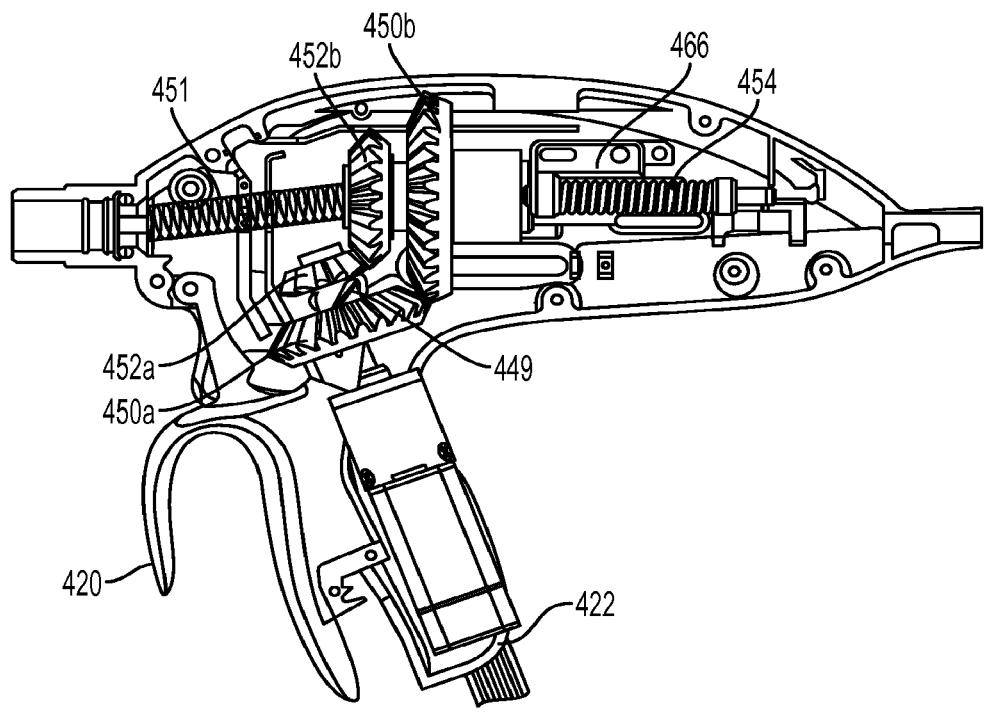
FIG. 10B is a partially transparent side view of the device of FIG. 10A after a compression member gear has translated away from the closure gear.
Figure 10C:
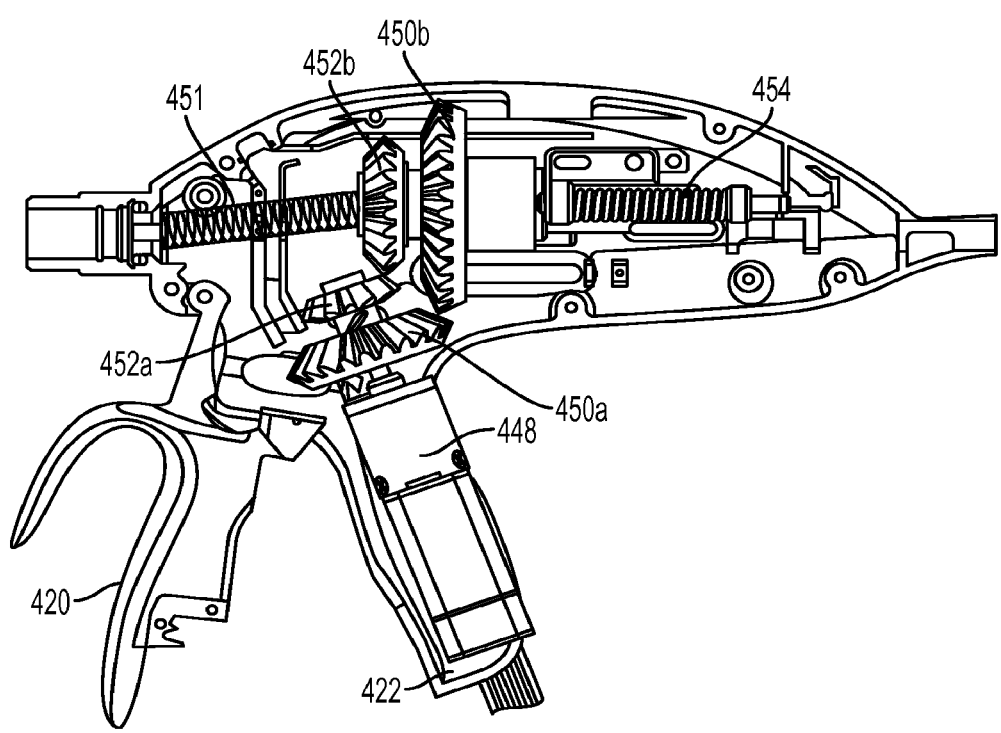
FIG. 10C is a partially transparent side view of the device of FIG. 10A after compression and cutting of tissue in the jaws, when the compression spring has returned to its first, resting position.

FIGS. 10A-10C illustrate various positions of the surgical device 400 having the bendix mechanism 492 and the components disposed in the housing 410 when the device 400 is in use. FIG. 10A shows the closure actuator 420 positioned adjacent to the stationary handle 422, which forces the first compression gear 450a into mesh with the second compression gear 450b via movement of the jaw closure actuator 420 acting on the first compression gear 450a to move away from the motor 448. When the gears 450a, 450b are so positioned, the motor 448 can cause both the first compression gear 450a and the first blade advancing gear 452a to rotate, the first and second compression gears 450a, 450b being in mesh while the first and second blade advancing gears 452a, 452b are not in mesh. Rotation of the first compression gear 450a can drive the slidable member 466 proximally to compress the compression spring 454, the spring 454 in turn applying a proximal tension to a jaw closure tube 451 for opening and closing the jaws (not shown). The spring 454 compressive force increases as the slidable member 466 translates proximally and in turn, a spring (not shown) biasing the bendix 449 toward the motor is overcome, causing the bendix 449 to translate linearly through the first compression gear 450a and away from the motor 448 such that rotation of the bendix 449 no longer causes corresponding rotation of the first compression gear 450a. As the bendix 449 moves in this direction, the blade advancing gears 452a, 452b come into mesh, as shown in FIG. 10B.

Continued rotation of the motor 448 rotates the blade advancing gears 452a, 452b and drives the cutting member (not shown) forward, toward a distal end of the jaws. The first compression gear 450a no longer rotates because the bendix helix 492 is now positioned above the first compression gear 450a. A bendix plate 449p can be positioned under the bendix 449 by the spring that previously compressed the bendix 449. This spring is sized and formed from a material that has a desired spring constant so that the first and second blade advancing gears remain in mesh as the cutting member is advanced distally toward the jaws.

After the cutting member has advanced distally toward a distal end of the jaws and has retracted proximally until it reaches its initial position, a user can unlatch the closure actuator 420 from the stationary handle 422 or the closure actuator 420 automatically begin to move away from the stationary handle 422 after the firing stroke is complete. This reverses the motor 448 and causes the drive shaft 448s to rotate in an opposite direction, retracting the bendix 449 down into the first compression gear 450a. When the bendix 449 is so positioned, the first compression gear 450a is driven in reverse and this retracts the sliding member 466 distally and relieves compression on the compression spring 454. As the closure actuator 420 continues to open, the system returns to the initial state shown in FIG. 10C, during which the spring 454 is in a resting configuration and the corresponding compression gears 450a, 450b and blade advancing gears 452a, 452b are no longer in mesh.

Figure 11:
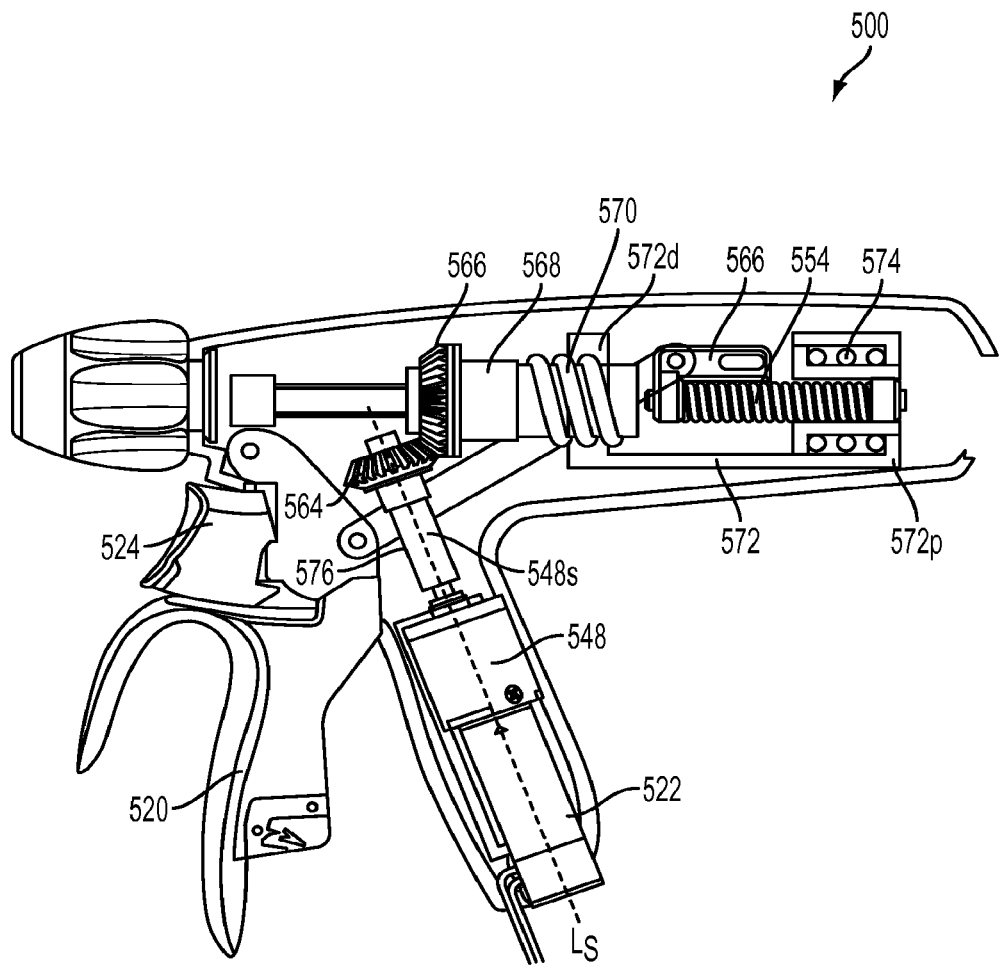
FIG. 11 is a partially transparent side view of an exemplary embodiment of a surgical device having power-assisted jaw closure and configured to adjust compression of tissue in jaws of an end effector (not shown) as energy is applied to the tissue.

FIG. 11 is another embodiment of a surgical device 500 having a mixed manual and automated, powered jaw closure. In accordance with this embodiment and many of the other embodiments provided for herein, a user mechanically applies a load to the device, and assistance is provided by the automated, powered portion of the device to provide a greater compression force to the tissue than would otherwise be possible by a purely manual closure device. More particularly, once the motor is activated, more of the stored potential energy is applied to the tissue, resulting in the form of greater compression. As shown, the housing 510 can include a motor 548, a shaft 548s, a first bevel gear 564, and a second bevel gear 566. As in some of the embodiments previously described, the motor 548 can include a rotatable shaft 548s having the first bevel gear 564 disposed thereon, the shaft being axially aligned with the longitudinal axis Ls of the motor 548 and of the stationary grip 522. The first bevel gear 564 can mesh with a second bevel gear 566 disposed at an angle relative to the first bevel gear 564 to transfer rotation to a different location in the housing 510, the angle being in the range of about 45 degrees to about 90 degrees.

A rotatable housing 568 can be coupled to a proximal end of the second bevel gear 566 and can be configured to rotate as the second bevel gear 566 is rotated. An outer surface of the rotatable housing 568 can include threads 570 formed thereon that can transfer rotation of the housing 510 into axial translation. As in the previous embodiment, a compression spring 554 can be mated with a slidable member that translates axially within the housing to compress the spring. For example, the threads 570 on the rotatable housing 568 can mate with a sled 572 that couples two components together. More specifically, a distal end 572d of the sled 572 can mate with the threads 570 on the rotatable housing 568 and a proximal end 572p of the sled 572 can mate with a force-limiting, counterbalance spring 574 disposed around a proximal end of the compression spring 554. The housing 510 can also include a linkage 576 extending between the closure actuator 520 and the slidable member 566 so that when a user moves the closure actuator 520 toward the stationary handle 522, the slidable member 566 moves proximally and compresses the compression spring 554.

In use, the counterbalance spring 574 can limit a force that the jaws apply to tissue when the jaws are closed. In general, the closer the jaws are approximated the greater the counter balancing force exerted by spring 574. While this force can vary, it can generally be in the range of about 5 to about 10 pounds of force measured at a distal-most end of the jaws. As the motor 548 is activated, the rotatable housing 568 can rotate and the sled 572 can move distally to relax a compression force applied to the counterbalance spring 574, allowing the force applied to the tissue by the jaws to increase over time. By using the motor 548 to relax the counterbalance spring 574, size and power requirements of the motor 548 can be reduced compared to a motor used to directly compress a compression spring. As in the previous embodiments, the compression and counterbalance springs 554, 574 can have various sizes and can be formed from various materials to achieve a desired spring constant. In some exemplary embodiments, the springs 554, 574 can be made from High Carbon Steel alloy (Music Wire) per ASTM A228, Stainless Steel Type 301/302/304 or Type 316, the springs can have a length in a neutral position (i.e., neither compressed nor expanded) approximately in the range of about 25 millimeters to about 50 millimeters, although the length can be longer provided the size of the device can accommodate the desired length, and can have a spring constant approximately in the range of about 20 N/mm to about 35 N/mm, although this value can also be smaller or larger, depending, at least in part, on a desired free length, precompression, and mechanical advantage. In some embodiments, the spring 574 can have a spring constant that is approximately 66 percent of the value for the spring constant of the spring 554. This comparison value, however, can vary a significant amount depending, at least in part, on the length of thread 570, the free lengths of the springs 554 and 574, and the state that the springs start in, e.g., if the springs start in a precompressed state, then the spring rate for the spring 574 can be as low as possible so long as it is provided a force of about 10 pounds. As a result, the amount of force needed to compress tissue in the jaws is reduced. For example, the amount of force needed to compress tissue is approximately in the range of about 22 Newtons to about 45 Newtons for thinner tissue, and approximately in the range of about 66 Newtons to about 90 Newtons for thicker tissue. In one exemplary embodiment, the starting compression for thinner tissue is approximately 22 Newtons when measured at a location more distal on the jaw, and a more full load of approximately 75 Newtons for thicker tissue. A person skilled in the art will be able to determine the appropriate spring constant and configurations of the springs that can be selected to achieve these values.

Tissue Sensing

Methods for sensing tissue are provided and generally include sensing a thickness and/or type of tissue grasped by jaws of a surgical device and adjusting operational parameters of the device in response to this mechanical feedback from the jaws to facilitate achieving hemostasis in the tissue. A person having skill in the art will recognize that the various mechanical feedback mechanisms provided for herein are distinguishable from electrical feedback mechanisms, which use electrical signals to measure various tissue parameters.

The devices herein can utilize a single motor for compression of tissue, including compression of springs to reduce the compressive force needed to actuate the device as described herein, and to sense tissue load. For example, the surgical device can include a sensor that can obtain a motor torque reading and a generator that can produce variable levels of energy, e.g., RF energy, which can be applied to tissue via the jaws. In use, a user can move the closure actuator toward the stationary handle to control an angle between the first jaw and the second jaw. When the closure actuator is positioned adjacent to the stationary handle, a latch (not shown) can hold the closure actuator in this position and can activate the motor. Activation of the motor can compress one or more compression springs, as in the embodiments described above, so that the jaws compress tissue disposed therein. The motor torque reading can provide an indication as to tissue thickness/toughness, with a higher motor torque reading being indicative of thicker and/or stronger tissue. The energy applied can be directly proportional to the torque value. In some embodiments, a sensor on a compression and/or cutting member, such as an encoder on the shaft used to advance the cutting member, can be used to indirectly approximate the jaw gap, for instance by determining a relative position of the cutting member during closure. As a result, the peak energy applied can be capped using an inverse relationship to the percent of full closure, in turn reducing the amount of energy applied and reducing the amount of thermal spread.

With the jaws so positioned, a first amount of RF power can be applied to the tissue. As a cutting member is advanced distally toward a distal end of the jaws, the device can monitor a position of the cutting member and can decrease the amount of RF power applied as the cutting member moves distally. When the cutting member is at its distal-most position relative to the jaws, a second amount of RF power can be applied to the tissue that is less than the first amount. As a result, the first amount of RF power is the maximum amount delivered to the tissue before the cutting member is advanced, which can allow for faster transection of the tissue. As the cutting member advances distally, the RF power decreases to minimize thermal spread in the tissue.

The devices herein can also control compression applied to the tissue based on a sensed impedance of the tissue. For example, the surgical device can include the closure actuator that can be moved toward the stationary handle to manually close the jaws. This can cause the jaws to apply a low initial compression force to tissue disposed therein. A user can activate a generator so that the jaws apply energy to the tissue. One or more sensors can be used to monitor an impedance of the tissue. If the impedance exceeds a predetermined threshold impedance, then the device can activate the motor to recompress the compression spring(s), thereby increasing the compression force applied by the jaws. If the impedance is less than or equal to the predetermined threshold impedance, then the device can continue to apply the current amount of compression until the impedance achieves the predetermined threshold. Impedance measurements can be taken throughout the duration of the surgery, thereby allowing the surgeon to adjust the amounts of compression being supplied to tissue based on the real-time feedback the surgeon receives.

A variable compression force can be applied to tissue prior to cutting and/or sealing the tissue and a tissue response can be monitored so that tissue type and thickness can be identified. As in the embodiments above, based on this feedback, the device can adjust operational parameters in order to facilitate hemostasis in the tissue. For example, the amount of compression, or pre-compression supplied by springs, can be adjusted in real time in response to the determined tissue type. By way of non-limiting example, in embodiments like those described above that include power-biased compression springs, the displacement of those springs, which in turn correlates to the change in threshold force, can be adjusted based on the thickness of tissue identified by the sensing mechanisms provided for herein.

Figure 12A:
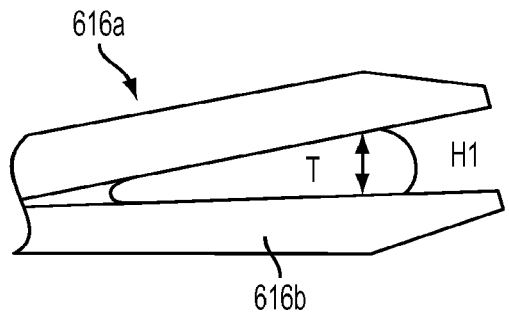
FIG. 12A is a side view of one exemplary embodiment of first and second jaws of a surgical device, the jaws having tissue grasped therebetween.
Figure 12B:
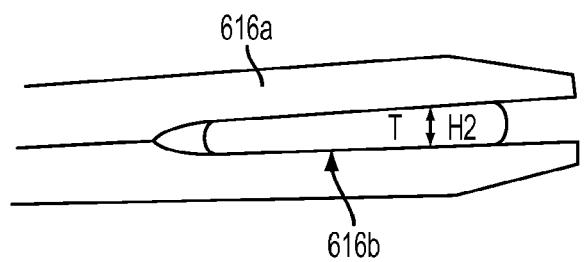
FIG. 12B is a side view of the jaws of FIG. 12A when the jaws have moved closer together to further compress the tissue therebetween.

FIGS. 12A and 12B illustrate exemplary jaws 616a, 616b grasping tissue in two different angular positions. FIG. 12A is a side view of the first and second jaws 616a, 616b of a surgical device in a first position where tissue T is grasped. The jaws 616a, 616b are spaced apart by a distance $H_1$ measured between a first point on an inner surface of the first jaw and a second point on an inner surface of the second jaw. FIG. 12B is a side view of the jaws 616a, 616b in a second position where the jaws 616a, 616b have moved closer together and further compress the tissue T. As shown, the jaws are spaced apart by a distance H₂ that is measured between the first and second points, H₂ being less than H₁.

Figure 13A:
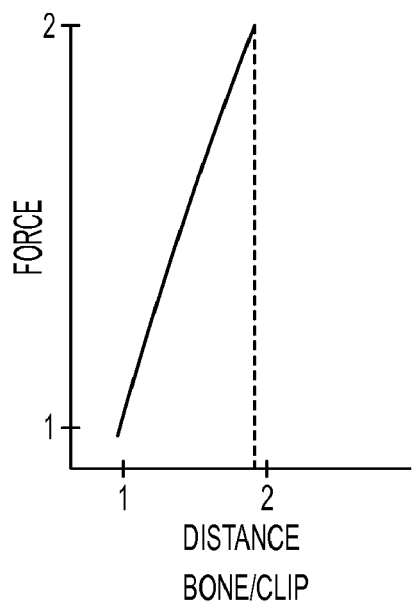
FIGS. 13A-13C are graphs illustrating the force jaws provided for herein apply to tissue disposed between the jaws relative to a distance between the jaws various materials disposed between the jaws.
Figure 13B:
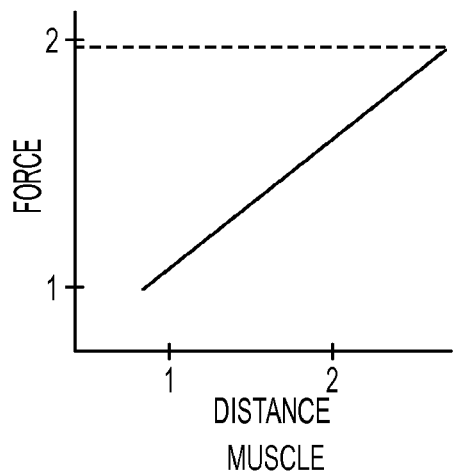

FIGS. 13A-13B are graphs of force that the jaws 616a, 616b apply to tissue versus the distance between the jaws for bone and various types of tissue. A surgical device for sensing tissue can include a processor that can analyze this data and operational parameters of the motor to determine a type of tissue grasped by the jaws. For example, the processor can calculate a slope M of the graphs using the following equation for calculating tissue spring rate:

$$M = \frac{F2 - F1}{H2 - H1}$$

The distances H₁ and H₂ and the forces F₁ and F₂ applied by the jaws 616a, 616b can be determined in various ways, such as based on the torque from the motor, an angular encoder, or other linear or rotary analog to digital mechanism. The processor can access a stored database of slope ranges for different types of tissue and bone, such as bone, muscle, mesentery, and fat/vessels. The processor can compare the stored ranges to the calculated slope in order to identify the type of tissue grasped by the jaws. Objects, such as surgical staples, can also be sensed and recognized. In some embodiments, the device can automatically adjust operational parameters based on the tissue type, such as a speed of the cutting member, amount of energy applied to the tissue, etc.

Figure 13C:
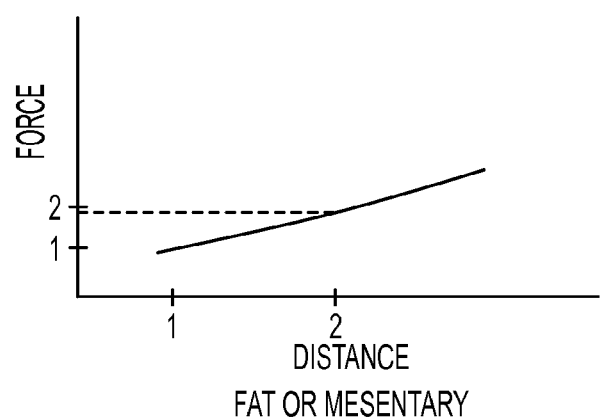

FIG. 13A illustrates a graph of force relative to distance between the jaws that has a steep slope indicative of bone and/or a staple being disposed in the jaws. Bone, staples, clips, and other hard surfaces provide greater resistance against the force applied by the jaws than softer material, such as fat or muscle. This concept can be seen in the graphs of force relative to distance shown in FIGS. 13B and 13C. In FIG. 13B, the slope of the graph of force relative to distance between the jaws is less than the slope in FIG. 13A. This indicates that the force applied when the jaws are in the second position and contacting muscle is less than the force applied when the jaws are in the second position and contacting bone. In FIG. 13C, the slope of the graph of force relative to distance between the jaws is less than the slope of the graphs of FIGS. 13A and 13B. This indicates that the force applied when the jaws are in the second position and contacting fat or mesentery is less than the force applied when the jaws are in the second position and contacting either bone or muscle. Based on this data, a processor can calculate slope of force relative to distance between the jaws and can compare the slope to a database of known slopes in order to identify the tissue or other object being engaged by the jaws.

Figure 14A:
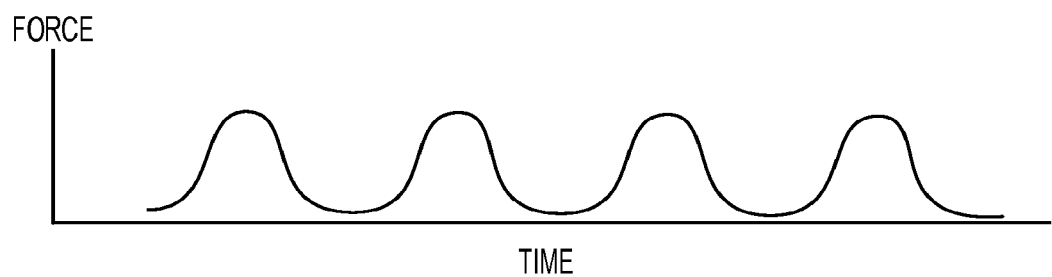
FIGS. 14A-14C are graphs illustrating a cyclical force jaws provided for herein apply to tissue disposed between the jaws relative to elapsed time.
Figure 14B:
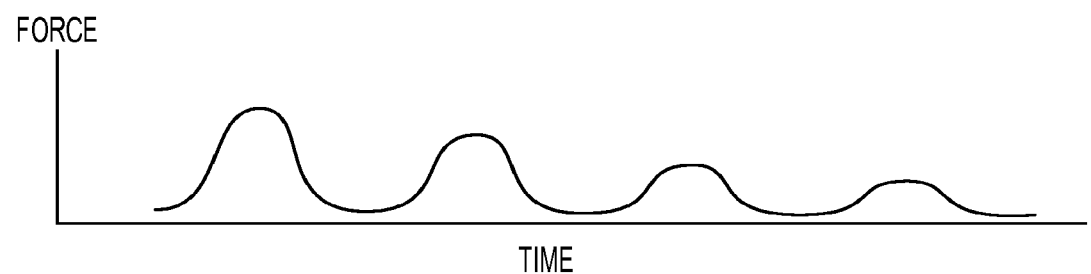
Figure 14C:
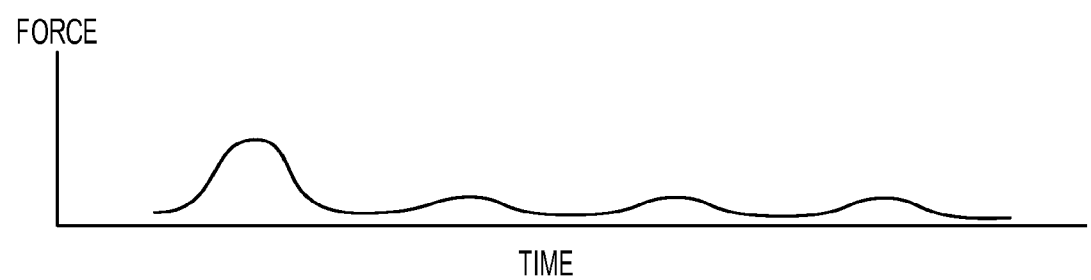

Another exemplary method for sensing tissue is provided in FIGS. 14A-14C which are graphs of a cyclical opening and closing action applied by jaws to tissue versus time for various types of tissue and bone. The peaks in the graphs indicate a peak force applied to tissue. In this embodiment, a surgical device can be configured to pulse tissue by opening and closing the jaws approximately 0.02 inches to full close and to sense the recovery of the tissue over time. For example, FIG. 14A illustrates a graph of force over time that is in the form of a wave having a substantially constant frequency and substantially constant maximum amplitude. This is consistent with tendon, which deforms when the force is applied and then springs back to an initial position. FIG. 14B illustrates a graph of force over time that is in the form of a wave having a maximum amplitude that decreases over time. This is consistent with softer tissue such as a small bowel, which weakens after repeated application of a compression force. FIG. 14C illustrates a graph of force over time that is in the form of a wave that rapidly decays over time and is the softest of the three types of tissue sensed in FIGS. 14A-14C. Based on this data, a processor can calculate a tissue spring rate and compare it to a database of known tissue spring rates in order to identify the tissue.

The identification of tissue can be used to adjust the speed of the cutting member, to adjust the clamping force applied by the jaws, or to control an amount of energy applied to the tissue by the jaws. In the illustrated embodiment, a surgical device can be selectively adjusted so that a speed of the cutting member through the tissue in FIG. 14A can be less than a speed of the cutting member through the tissue in FIGS. 14B and 14C because the tissue in FIG. 14A has a higher resistance to being compressed. This can help ensure that the cutting member does not jam when it is translating through the tissue.

Cyclical compression can be applied to tissue during various stages of jaw closure and firing of the cutting member. For example, tissue can be pulsed by the jaws prior to advancing the cutting member through tissue disposed in the jaws. For another example, tissue can be pulsed after the tissue has been sealed, or as the cutting member is retracted proximally at the end of a firing stroke. The tissue spring rate after sealing can be indicative of a quality and strength of the seal and can be used to determine whether additional energy should be applied to the tissue to increase the quality of the seal.

Exemplary Surgical Methods

The devices herein can be used to perform a surgical procedure in which tissue is grasped and transected, and optionally sealed using applied energy. As will be appreciated, while reference is made below to particular features of a device for performing the surgical procedure, the devices can include any combination of the features described above. A person skilled in the art will further appreciate that the procedure can be a minimally invasive procedure or an open surgical procedure. The devices herein can also be used for robotic-assisted minimally invasive or open procedures. The procedure usually begins by preparing the patient for surgery and making one or more appropriately sized incisions at a desired location. In a minimally invasive procedure, one or more cannulas or trocars (not shown) can be positioned in the incisions to provide access to the surgical. One or more viewing devices, e.g., scopes, can be placed in one of the incisions to allow medical personnel to view the surgical site from outside the body.

Once the patient is prepared for surgery, a surgical device can be inserted through the incision and/or through the cannula and the end effector can be positioned adjacent to a desired tissue to be treated. In an exemplary embodiment, the tissue to be treated can include one or more layers of blood vessels. As the surgical device is being inserted into the patient, the closure actuator can be disposed adjacent to the stationary handle in which the jaws 16a, 16b are in a closed position so that the jaws have a smaller width that can be inserted into a small access channel. When the jaws 16a, 16b are positioned adjacent to the tissue to be treated, the closure grip 20 can be moved away from the stationary grip 22 and the tissue to be treated can be positioned between the jaws 16a, 16b. Movement of the closure grip 20 toward the stationary grip 22 can close the jaws 16a, 16b so that tissue is securely grasped between the jaws 16a, 16b. An angular position of the jaws 16a, 16b can directly correspond to an angular position of the closure actuator 20 relative to the stationary handle. As previously described, the devices can include one or more springs, such as the compression springs 360a, 360b shown in FIG. 5C, and these springs can increase a compressive force that the jaws apply to tissue disposed therein compared to manual, mechanically actuated jaws that do not utilize power-biased compression springs.

As a user applies an input pressure to the closure actuator to move it relative to the stationary handle, a sensor, such as a Hall Effect sensor, proximity sensor, switch, potentiometer, encoder, or the like can measure a distance between the jaws. The processor can calculate a force applied to the tissue grasped between the jaws 16a, 16b. With the position of the jaws 16a, 16b fixed and having tissue grasped therebetween, a user can engage a firing actuator 24 that can advance the cutting member and/or compression member to cut the tissue. In another embodiment, upon closure of the jaws, the device 100 can automatically advance a cutting member and/or a compression member toward the jaws 16a, 16b to cut the tissue disposed therebetween. A person skilled in the art will appreciate that energy can be selectively applied to the tissue prior to or during transection of the tissue disposed in the jaws 16a, 16b, as described in further detail below. As will also be appreciated, any of the tissue sensing methods described above can be used to determine a type of tissue/object grasped in the jaws and in response, the device can change the amount of compressive force applied to the tissue by the jaws by compressing or relaxing the power-biased compression springs described above to open or close the jaws.

The surgical device can be inserted into the body using the method described above, but can also apply energy, e.g., RF current, to tissue disposed between the jaws prior to, during, and/or after transection of the tissue. After the cutting member is advanced through the tissue and is retracted proximally, the device 200 can continue to apply energy to the cut tissue or the jaws 216a, 216b can automatically release the tissue. In either example, after the cutting is complete, the closure actuator, the firing actuator, and the jaws can release from the compressed/closed positions and can automatically return to their initial position so that the jaw closure, tissue compression, cutting, and/or sealing can be repeated as many times as desired. As mentioned above, tissue can be pulsed after the tissue has been sealed and/or as the cutting member is retracted proximally at the end of a firing stroke. The tissue sensing methods described above can be used to determine the tissue spring rate after sealing, which can be indicative of a quality and strength of the seal and can be used to determine whether additional energy should be applied to the tissue to increase the quality of the seal. Based on this feedback, if it is necessary, additional energy can be applied to the tissue to further seal the tissue.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical instrument, comprising:
   a jaw assembly having a first jaw and a second jaw pivotally coupled together, the first and second jaws having opposed tissue contacting surfaces configured to pivot towards each other to compress tissue therebetween when a force applied to at least one of the first and second jaws meets or exceeds a threshold force;
   a cutting member having a distal portion thereof disposed between the opposed tissue contacting surfaces of the first and second jaws, the distal portion including a cutting edge that extends between and substantially perpendicular to the first and second jaws;
   a housing having a motor, a first spring, and a counterbalance spring disposed therein, the motor being operatively coupled to the first spring such that the motor is configured to move the first spring from a first position to a second, compressed position to increase a force the jaws apply to the tissue, the first spring being in series with the counterbalance spring such that activation of the motor decreases compression on the counterbalance spring and increases compression of the first spring to compress tissue disposed in the jaws, and the motor further being operatively coupled to the cutting member such that the motor is configured to drive the cutting member distally through the first and second jaws; and
   a rotatable housing and a translation mechanism configured so that activation of the motor rotates the rotatable housing which moves the translation mechanism distally to compress the first spring.

2. The device of claim 1, further comprising a second spring operatively coupled to a closure actuator disposed in the housing such that when the closure actuator is activated, the second spring moves from a first position to a second, compressed position and the jaws apply a compressive force to the tissue.

3. The device of claim 2, further comprising a shaft extending between the housing and the jaw assembly and including a jaw closure tube having a proximal end operatively coupled to the second spring and a distal end coupled to a proximal end of the jaw assembly, the jaw closure tube being configured to move axially to close the jaws.

4. The device of claim 3, further comprising a cutting member advancing tube disposed in the shaft and having a proximal end operatively coupled to the first spring and a distal end coupled to a proximal end of the cutting member, the cutting member advancing tube configured to move axially to advance and retract the cutting member relative to the jaws.

5. The device of claim 1, wherein the motor is operatively coupled to the jaws such that activation of the motor is configured to close the jaws prior to the cutting member being advanced distally through the first and second jaws.

6. The device of claim 1, further comprising a drive mechanism operatively coupling the motor to the first spring, the drive mechanism including a lead screw having first and second threaded portions, the first threaded portion coupled to a first driving member for compressing the first spring and the second threaded portion coupled to a second driving member for advancing the cutting member within the jaws.

7. The device of claim 1, further comprising a first bevel gear and a second bevel gear disposed in the housing, the first bevel gear being in meshing engagement with the second bevel gear, the second bevel gear being disposed at an angle relative to the first bevel gear to transfer rotation to a different location in the housing.

8. The device of claim 7, further comprising a rotatable shaft extending between the motor and the first bevel gear.

9. The device of claim 7, further comprising a rotatable housing coupled to the second bevel gear and configured to rotate with rotation of the second bevel gear.

10. A surgical instrument, comprising:
a jaw assembly having a first jaw and a second jaw pivotally coupled together, the first and second jaws having opposed tissue contacting surfaces configured to pivot towards each other to compress tissue therebetween when a force applied to at least one of the first and second jaws meets or exceeds a threshold force;
a cutting member having a distal portion thereof disposed between the opposed tissue contacting surfaces of the first and second jaws, the distal portion including a cutting edge that extends between and substantially perpendicular to the first and second jaws;
a housing having a motor and a first spring disposed therein, the motor being operatively coupled to the first spring such that the motor is configured to move the first spring from a first position to a second, compressed position to increase a force the jaws apply to the tissue, and the motor further being operatively coupled to the cutting member such that the motor is configured to drive the cutting member distally through the first and second jaws; and
a drive mechanism operatively coupling the motor to the first spring, the drive mechanism including a lead screw having first and second threaded portions, the first threaded portion coupled to a first driving member for compressing the first spring and the second threaded portion coupled to a second driving member for advancing the cutting member within the jaws;

wherein the second driving member comprises a rack and first and second pinions coupled to the first spring such that when the motor is activated, the lead screw rotates and moves the second driving member distally toward the jaws, rotating the first and second pinions which move a distal end of the first spring proximally away from the jaws to compress the first spring.

11. The device of claim 10, further comprising a second spring operatively coupled to a closure actuator disposed in the housing such that when the closure actuator is activated, the second spring moves from a first position to a second, compressed position and the jaws apply a compressive force to the tissue.

12. The device of claim 10, wherein the motor is operatively coupled to the jaws such that activation of the motor is configured to close the jaws prior to the cutting member being advanced distally through the first and second jaws.

13. A surgical instrument, comprising:
a jaw assembly having a first jaw and a second jaw pivotally coupled together, the first and second jaws having opposed tissue contacting surfaces configured to pivot towards each other to compress tissue therebetween when a force applied to at least one of the first and second jaws meets or exceeds a threshold force;
a cutting member having a distal portion thereof disposed between the opposed tissue contacting surfaces of the first and second jaws, the distal portion including a cutting edge that extends between and substantially perpendicular to the first and second jaws; and
a housing having a motor and a first spring disposed therein, the motor being operatively coupled to the first spring such that the motor is configured to move the first spring from a first position to a second, compressed position to increase a force the jaws apply to the tissue, and the motor further being operatively coupled to the cutting member such that the motor is configured to drive the cutting member distally through the first and second jaws; and
a spring-loaded bendix mechanism having a compression gear and a blade advancing gear spaced axially apart, the bendix mechanism being configured to move away from the motor when the motor is activated, and the axial spacing between the compression gear and the blade advancing gear increasing during activation of the motor.

14. The device of claim 13, further comprising a rotatable housing and a translation mechanism configured so that activation of the motor rotates the rotatable housing that moves the translation mechanism distally to compress the first spring.

15. The device of claim 13, further comprising a second spring operatively coupled to a closure actuator disposed in the housing such that when the closure actuator is activated, the second spring moves from a first position to a second, compressed position and the jaws apply a compressive force to the tissue.

16. The device of claim 13, wherein the motor is operatively coupled to the jaws such that activation of the motor is configured to close the jaws prior to the cutting member being advanced distally through the first and second jaws.

* * * * *